(12) United States Patent
Bahar et al.

(10) Patent No.: US 12,076,490 B2
(45) Date of Patent: *Sep. 3, 2024

(54) ENVIRONMENT CONTROL SYSTEM UTILIZING AN ELECTROCHEMICAL CELL

(71) Applicant: FFI IONIX IP, INC., Wilmington, DE (US)

(72) Inventors: Bamdad Bahar, Georgetown, DE (US); Jacob Zerby, Dover, DE (US)

(73) Assignee: FFI IONIX IP, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,731

(22) Filed: Nov. 21, 2022

(65) Prior Publication Data
US 2023/0089056 A1  Mar. 23, 2023

Related U.S. Application Data

(63) Continuation of application No. 16/291,932, filed on Mar. 4, 2019, now Pat. No. 11,504,494, which is a
(Continued)

(51) Int. Cl.
*A61M 16/10* (2006.01)
*A61L 2/03* (2006.01)
(Continued)

(52) U.S. Cl.
CPC .......... *A61M 16/101* (2014.02); *A61L 2/035* (2013.01); *C25B 1/04* (2013.01); *C25B 9/23* (2021.01);
(Continued)

(58) Field of Classification Search
CPC .... C25B 1/04; C25B 1/00; C25B 1/10; C25B 9/10; C25B 9/12; C25B 9/19; C25B 9/21;
(Continued)

(56) References Cited

U.S. PATENT DOCUMENTS 10,890,344 B2 *  1/2021  Bahar .................. F24F 11/0008
11,504,494 B2 * 11/2022  Bahar ..................... A61L 2/035
11,717,788 B2 *  8/2023  Bahar ....................... F24F 3/14
                                                                204/230.2

* cited by examiner

*Primary Examiner* — Ciel P Contreras
(74) *Attorney, Agent, or Firm* — Invention To Patent Services; Alex Hobson

(57) ABSTRACT

An environment control system utilizes oxygen and humidity control devices that are coupled with an enclosure to independently control the oxygen concentration and the humidity level within the enclosure. An oxygen depletion device may be an oxygen depletion electrolyzer cell that reacts with oxygen within the cell and produces water through electrochemical reactions. A desiccating device may be g, a dehumidification electrolyzer cell, a desiccator, a membrane desiccator or a condenser. A controller may control the amount of voltage and/or current provided to the oxygen depletion electrolyzer cell and therefore the rate of oxygen reduction and may control the amount of voltage and/or current provided to the dehumidification electrolyzer cell and therefore the rate of humidity reduction. The oxygen level may be determined by the measurement of voltage and a limiting current of the oxygen depletion electrolyzer cell. The enclosure may be a food or artifact enclosure.

19 Claims, 23 Drawing Sheets

Related U.S. Application Data continuation-in-part of application No. 15/800,398, filed on Nov. 1, 2017, now Pat. No. 10,890,344, which is a continuation-in-part of application No. PCT/US2016/063699, filed on Nov. 23, 2016.

(60) Provisional application No. 62/638,292, filed on Mar. 4, 2018, provisional application No. 62/416,072, filed on Nov. 1, 2016, provisional application No. 62/385,175, filed on Sep. 8, 2016, provisional application No. 62/373,329, filed on Aug. 10, 2016, provisional application No. 62/363,545, filed on Jul. 18, 2016, provisional application No. 62/300,074, filed on Feb. 26, 2016, provisional application No. 62/258,945, filed on Nov. 23, 2015.

(51) Int. Cl.
| | |
|---|---|
| *A61L 9/015* | (2006.01) |
| *C25B 1/04* | (2021.01) |
| *C25B 9/23* | (2021.01) |
| *C25B 9/30* | (2021.01) |
| *C25B 9/73* | (2021.01) |
| *C25B 11/02* | (2021.01) |
| *C25B 13/00* | (2006.01) |
| *C25B 15/02* | (2021.01) |
| *F24F 11/00* | (2018.01) |

(52) U.S. Cl.
CPC ................ *C25B 9/30* (2021.01); *C25B 9/73* (2021.01); *C25B 11/02* (2013.01); *C25B 13/00* (2013.01); *C25B 15/02* (2013.01); *A61L 9/015* (2013.01); *A61L 2209/212* (2013.01); *F24F 11/0008* (2013.01); *Y02E 60/36* (2013.01)

(58) Field of Classification Search
CPC ... C25B 9/23; C25B 9/77; C25B 13/00; F24F 3/14; F24F 3/166; F24F 11/0008; F24F 2003/144; F24F 2003/1692
See application file for complete search history.

ENVIRONMENT CONTROL SYSTEM UTILIZING AN ELECTROCHEMICAL CELL

CROSS REFERENCE TO RELATED APPLICATIONS

This application is a continuation of U.S. patent application Ser. No. 16/291,932, filed on Mar. 4, 2019 and currently pending, which is a continuation in part of U.S. patent application Ser. No. 15/800,398, filed on Nov. 1, 2017 and currently pending which is a continuation in part of International Patent Application no. PCT/US2016/063699, filed on Nov. 23, 2016 which claims the benefit of U.S. provisional patent application No. 62/258,945, filed on Nov. 23, 2015, U.S. provisional patent application No. 62/300,074, filed on Feb. 26, 2016, U.S. provisional patent application No. 62/353,545, filed on Jun. 22, 2016, U.S. provisional patent application No. 62/373,329, filed on Aug. 10, 2016 and U.S. provisional patent application No. 62/385,175, filed on Sep. 8, 2016; and this application also claims the benefit of priority to U.S. provisional patent application No. 62/416,072, filed on Nov. 1, 2016, and this application claims the benefit of priority to U.S. provisional patent application No. 62/638,292, filed on Mar. 4, 2018; the entirety of all application listed above are hereby incorporated by reference herein.

BACKGROUND OF THE INVENTION

Background

There are many types of enclosures that require environment control wherein the oxygen and/or the humidity level is controlled. For example, museum artifacts and documents are often stored in environmentally controlled enclosures to reduce degradation due to oxidation, rust and the like. In addition, produce and other consumer products and goods may benefit from storage in environment controlled enclosures, including refrigerated items. Electrolyzer cells utilizing membrane electrode assemblies can be used in an electrolysis mode to reduce oxygen with an increase in humidity, or decrease humidity with an increase in oxygen. In most enclosure applications for valuables and produce however, it is desirable to reduce oxygen and also reduce humidity levels. There exists a need for an energy efficient, durable, quiet and effective environment control system for enclosures.

SUMMARY OF THE INVENTION

The invention is directed to an environment control system that employs an electrochemical cell(s) to effectively control oxygen and also control humidity within an enclosure. In one embodiment, oxygen concentration is reduced and humidity is reduced within an enclosure. In another embodiment, oxygen concentration is increased while humidity is increased. An exemplary environment control system utilizes oxygen and humidity control devices that are coupled with an enclosure to independently control the oxygen concentration and the humidity, RH, within the enclosure. An oxygen control device may be an oxygen depletion electrolyzer cell that reacts with oxygen and produces water through electrochemical reactions. In an alternate embodiment, an oxygen control device is operated as an oxygen increase device, wherein oxygen is produced within the enclosure from the reaction with water to form oxygen and protons. A dehumidification device may be a dehumidification electrolyzer cell, a humidification electrolyzer cell, a desiccator, a membrane separator, and/or a condenser. A controller may control the amount of voltage and/or current provided to the oxygen depletion electrolyzer cell and therefore the rate of oxygen reduction and may control the amount of voltage and/or current provided to the dehumidification electrolyzer cell and therefore control the rate of humidity reduction.

In an exemplary embodiment, an environment control system is coupled with an enclosure and comprises an oxygen depletion electrolyzer cell that reduces the oxygen concentration in an enclosure. An oxygen depletion electrolyzer cell comprises an ion conducting material, such as an ionomer that transports cations or protons from an anode and a cathode, wherein the anode and cathode are configured on opposing sides of the ionomer. The cathode is in fluid communication with the enclosure and a power source is coupled with the anode and cathode to provide an electrical potential across the anode and the cathode to initiate electrolysis of water. Water is reacted to form oxygen and protons on the anode and the protons are transported across the ionomer, or cation conducting material, to the cathode where these protons react with oxygen at the cathode to form water, thereby depleting oxygen on the cathode side while producing water on the cathode side. As described herein, novel system configurations are employed to reduce and control the humidity within the enclosure that may be produced, at least in part, by the cathode of the oxygen depletion electrolyzer cell.

An exemplary environment control system may comprise an oxygen increase electrolyzer cell, wherein the anode is configured in fluid communication with the enclosure and produces oxygen from the reaction of water at the anode. An oxygen control electrolyzer cell may be run in either an oxygen depletion mode or an oxygen increase mode, depending on the potential applied across the anode and the cathode.

An exemplary environment control system comprises a humidification control device, such as a dehumidification device that reduces the humidification level of the enclosure either directly or indirectly. In an exemplary embodiment, the dehumidification device is a dehumidification electrolyzer cell that pumps water out of the enclosure or out of a conditioner chamber, or the humidity control portion of the conditioner chamber. Other dehumidification devices include a separator, such as a separator membrane that allows moisture to pass therethrough, but is substantially air impermeable and therefore prevents oxygen flow. A separator that is substantially air impermeable has no bulk flow of gas through the thickness of the separator and may have a Gurley Densometer time of 100 seconds or more, Model 4110N from Gurley Precision Instruments, Troy NY, for example. Other dehumidification devices include desiccants, condensers and any combination of the dehumidification devices described.

An exemplary environmental control system comprises a humidification electrolyzer cell, wherein the electrolyzer cell is run with the cathode in fluid communication with the enclosure or with the humidity control portion of a conditioning chamber. In one embodiment, a humidification electrolyzer cell produces moisture in a conditioner chamber and a separator membrane transfers this moisture to an oxygen control chamber.

In an exemplary embodiment, the oxygen control and/or the humidification electrolyzer, comprises an ionomer, such as a perfluorosulfonic acid polymer. The ionomer may be a composite comprising a support material that is coated and/or imbibed with the ionomer. The ionomer may be very thin, such as less than 25 microns, less than 20 microns and more preferably less than 15 microns. A thin ionomer is preferred as it will allow for higher rates of proton transport and better efficiency.

In an exemplary embodiment, a conditioner chamber is utilized to dehumidify gas that is introduce into the enclosure. A conditioner chamber, or portion thereof is in fluid communication with the enclosure and there may be one or more valves and/or fans or other air moving device to move gas between the conditioner chamber and the enclosure. In an exemplary embodiment, a conditioner chamber is separated into an oxygen control chamber and a humidity control chamber. A separator membrane may be configured between the oxygen control chamber and the humidity control chamber and allow humidity to pass from one chamber to the other. This separated conditioner chamber can effectively reduce humidity in the oxygen control chamber while simultaneously reducing humidity in the oxygen control chamber. When the oxygen control chamber is at a higher humidity level than the humidity control chamber, water vapor will be transferred through the separator membrane to the humidity control chamber, due to concentration gradients. The humidity control chamber may reduce the humidity level through one or more dehumidification devices, as described herein. For example, a dehumidification electrolyzer cell may pump water out of the humidity control portion to maintain a very low level of humidity in the humidity control chamber, and therefore draw moisture from the oxygen control chamber through a separator. A separator may comprise an ionomer membrane and again, the ionomer membrane may be a reinforced ionomer membrane having a support material. A separator or moisture transmission material may be pleated or corrugated to provide a higher surface area of the opening to the enclosure. An exemplary separator is an ionomer, such as Nafion® membrane, from E.I. DuPont, Inc, Wilmington, Delaware, or Gore-Select® membrane from W.L. Gore and Associates, Inc., Newark, Delaware.

An oxygen control chamber, or a portion thereof, may be configured as an exchange conduit having an inlet from the enclosure and an outlet back into the enclosure. An exchange conduit may comprise a separator for transfer of moisture from the oxygen control chamber or exchange conduit to the humidity control chamber. An exchange conduit may extend within the conditioner chamber or the humidity control portion of the conditioner chamber and may be nested, such as having additional length configured therein. An exchange conduit may be nested by having a serpentine configuration, a coiled configuration, a pleated configuration and a back and forth configuration. When a separator is configured on the exchange conduit, this nested configuration greatly increase the surface area for moisture transfer to the humidity control chamber.

An exemplary environment control system may reduce humidity levels in the humidity control chamber through one or more dehumidification devices, as described herein. A desiccant may be configured to absorb moisture in the humidity control chamber and may be configured in a dehumidification loop, a conduit with an inlet and outlet coupled with the humidity control chamber. A fan or other air moving device may be used to force a flow of gas from the humidity control chamber through the humidity control chamber. In this way, moisture can be removed actively, by initiating the flow of humidity control chamber gas through the dehumidification loop, versus a passive dehumidification, wherein a desiccant is simply within the humidity control chamber. Any suitable desiccant may be used including silica gel and the like. In addition, a desiccant or desiccator may comprise a heater to drive off absorbed moisture and a set of valves may allow this expelled absorbed moisture to be expelled from the system, thereby rejuvenating the desiccant.

An exemplary environment control system may reduce humidity levels in the humidity control chamber through a condenser. Again, a condenser may be configured within the humidity control chamber or within a dehumidification loop of the humidity control chamber. In addition, a condenser may produce condensed liquid water that can be expelled from the system through a valve or may be provided to a water chamber that is in fluid communication with the anode of the oxygen depletion electrolyzer cell. The anode on the oxygen depletion electrolyzer cell reacts water to from oxygen and protons.

An exemplary environment control system may reduce humidity levels in the humidity control chamber through a separator, such as an ionomer membrane separator, as described herein. The separator may be configured between the humidity control chamber and the outside environment and may transfer moisture from the humidity control chamber to the outside environment when the humidity level within the humidity control chamber is greater than the humidity level in the outside ambient environment.

An exemplary environment control system may reduce humidity levels in the humidity control chamber through a humidity control electrolyzer cell having an anode in fluid communication with the interior volume of the humidity control chamber and a cathode exposed to the outside ambient environment. Water or humidity within the humidity control chamber will react on the anode to form oxygen and protons. The protons are transferred across or through the ionomer membrane and react with oxygen on the cathode to reform water. In addition, water molecules are drug along with the flow of protons from the anode to the cathode. A control system may monitor the humidity level within the humidity control chamber, the oxygen control chamber and/or the enclosure and then control the voltage potential across the anode and cathode of the dehumidification electrolyzer cell of the humidity control chamber.

An exemplary environment control system may comprise a fuel loop, or a conduit that directs gas from the humidity control chamber to the anode side of the oxygen depletion electrolyzer cell and then back to the humidity control chamber. A fuel loop reduces humidity in the humidity control chamber by reaction of water in the fuel loop on the anode of an oxygen depletion electrolyzer cell and may be considered a dehumidification device, as used herein. A fan and one of more valves may be used to provide a flow of gas from the humidity control chamber through the fuel loop and the anode on the oxygen depletion electrolyzer cell may also receive gas or air from the ambient environment outside of the conditioner chamber.

A control system of an exemplary environment control system may comprise one or more sensors, such as an oxygen, humidity, and/or temperature sensor that are configured in the conditioner chamber, the oxygen control chamber, the humidity control chamber and/or the enclosure or conduits to and from the enclosure. The control system may receive input from these sensors and may then control the power level, voltage potential and/or current to the electrolyzer cells to adjust the humidity and/or oxygen levels as required. A user input feature may be used to set an oxygen and/or humidity level and/or limits for the system, such as for the enclosure and the control system, utilizing a processor or micro-processor may then control fans, valves, the power supply to the electrolyzer cells and the like to maintain the user input levels or set points. In addition, data may be collected by the control system and transferred to a secondary location. For example, a removable memory device, such as a thumb drive may be attached to the environment control system to collect data including sensed values of temperature, humidity levels, and oxygen concentration, as well as voltages applied to the electrolyzer cell or cells and the like. The thumb drive could be removed for download on a secondary electronic device or computer. In still another embodiment, an exemplary environment control system comprises a wireless signal transmitter for transmitting the data wirelessly to a secondary location, such as a computer or server. An exemplary environment control system may comprise a wireless signal receiver for receiving set point values for temperature, humidity and/or oxygen concentration and may receive commands including voltage potential inputs for an electrolyzer.

Any number of filters and/or valves may be used to control gas or air flow into or around the environment control system. Filters may be configured to the conditioner chamber to prevent contaminates from poisoning the electrolyzer cells. Filters may be configured on inlet and outlets to the enclosure. In addition, desiccators may be configured on air or gas inlets to the conditioner chamber, the oxygen control and/or humidity control chambers.

In one embodiment, a fan is configured to produce a flow of process air onto an electrode of an electrolyzer. In an exemplary embodiment, a membrane electrode assembly (MEA) fan blows onto an electrode, wherein the flow of air is substantially perpendicular, within about 30 degrees of perpendicular, or within about 20 degrees or more preferably within about 10 degrees of perpendicular to the plane of the electrode. It has been found that this greatly increase the performance of the electrolyzer. A fan blowing process air directly onto the anode of an electrolyzer cell has been shown to increase the performance by more than 200 percent. This force air flow onto the anode may remove boundary layers that can reduce reaction rates.

There are many different applications wherein the control of oxygen concentration and/or relative humidity levels, RH are required or desired. Many enclosures are configured to control these environmental parameters including, but not limited to, safes or enclosures for valuable items that may be damaged by prolonged exposure to high humidity, such as documents, artifacts, jewels, jewelry, weapons, guns, knives, currency and the like. In addition, there are applications where a flow of air having a controlled level of oxygen and/or humidity are desired, such as a Positive Airway Pressure, PAP, device, a respirator, an oxygen respirator and the like. A PAP device provides a pressurized flow of air to a person to aid in effective breathing while sleeping. An environment control system, as described herein, may provide additional humidity and/or oxygen to the flow of air in a PAP device. In addition, there are articles, such as produce, that may be located in an enclosure wherein the control of oxygen level is desired or beneficial. A reduced oxygen level in a refrigerator compartment for produce may prevent the produce from spoiling or going bad. In addition, some enclosures may have a controlled and reduced level of oxygen to kill organisms.

An object of the present invention is to provide independent control of oxygen concentration and humidity level within an enclosure utilizing at least one electrolyzer cell. An exemplary object of this invention is to provide oxygen depletion without an increase in relative humidity to an enclosure or a decrease humidity level of the enclosure.

Another exemplary object of this invention is to provide an increased oxygen and humidity level to an enclosure or air flow.

The present invention relates to electrolyzer technology with advanced preserving capabilities for valuables, artifacts, or food items. An exemplary electrolyzer cell is a polymer electrolyte membrane with catalyst and current collectors on both sides with a housing. An electrolyzer cell is typically used while in contact with liquid water to generate oxygen on the anode and hydrogen on the cathode. When used in the open air with no available liquid water, they rely on the available water vapor or humidity in the air.

Oxygen reduction is very desirable to prevent oxidation, to kill genus and bug infestations, preserve food, valuable artifacts and to prevent a fire from originating inside the enclosure. Separately, controlling the humidity is just as important. There are disadvantages to running an electrolyzer cell without independent control of the humidity and oxygen levels. One is that you will likely reach 100% RH in an enclosure before removing all of the oxygen. The other is the lack of precise independent control over either of the conditions. The ideal humidity and oxygen level varies depending on what is being preserved inside the enclosure. One way to achieve precise control is to remove moisture separately with another form of dehumidification or to use an electrolyzer cell in reverse while sealing it off from the enclosure. The seal could consist of a window with a membrane that allows moisture to pass through but not gases, including oxygen. This type of independent control of humidity and oxygen removal requires a way to measure the contents of the enclosure. You also need to be able to independently control the humidifying and dehumidifying system with electronics. The integrity of the seal and the conditions outside the enclosure play a role in the efficiency.

An enclosure, as described herein, includes but is not limited to humidors, refrigerator or freezer sub-compartments, museum displays, gun storage, musical instrument storage, paper storage, and storage of a host of moisture sensitive products such as fossils, ancient artifacts, stamps, bonds, etc. as well as shipping containers. An exemplary control system may be sized to meet the demands of the enclosure. A larger enclosure will require a larger oxygen depletion electrolyzer cell area than a smaller enclosure. An enclosure may be on the order of 0.1 $m^3$ or more, 0.5 $m^3$ or more, 1 $m^3$ or more, 5 $m^3$ or more, 12 $m^3$ or more or no more than about 12 $m^3$ or no more than about 5 $m^3$, no more than 3 $m^3$ and any range between and including the volumes provided.

An exemplary environment control system, may comprise a remote monitor for an enclosure, and may comprise wireless monitoring of the enclosure conditions including humidity level and oxygen concentration or level. The enclosure environmental conditions may be sent to a remote electronic device, such as a mobile telephone, tablet computer or computer. A user may change the desired set points of humidity, temperature and oxygen level of the enclosure. Wireless transmission may also allow a remote electronic device to record the enclosure parameters, temperature, humidity and oxygen level. In addition, a user may receive an alert if there are significant changes in the enclosure environment parameters or if one of the parameters fall moves outside of a threshold value for one of the set points.

There is recognition that in some cases reactant gases must be inside the enclosure. The enclosure may not always be in a hermetically sealed system, i.e. some leakage in and out of the enclosure is an option. In addition, the system can be controlled with a sensor inside the device, in others the system is simply switched on and off for a limited duration.

An exemplary control system comprises an oxygen and humidity control system that can be used in combination with other systems. For example, it has been found that using Spanish cedar with a humidity control device provides humidity buffering. Also, it has been found that using a silica gel in combination with a humidity control device also provides humidity buffering. And there are some advantages because if electricity is switched off, or if for some reason the system under or over humidifies—the buffer can compensate. A silica gel or other hygroscopic material may be placed within an enclosure to provide this moisture buffering. Some hygroscopic materials have a humidity level range wherein the absorb or release moisture when the RH goes above the range or drops below the range, respectively.

Utilizing electrolyzer technology in a cell to move moisture while relying on ambient air conditions can be challenging. The environment providing the moisture can be dry reducing the power output of the cell in either direction. There is also a reduction in performance when this sort of device is used in a cold environment like inside a refrigerator. Therefore, it is of the utmost importance to optimize the cell's electrical contact characteristics with the catalyst. It is also an advantage to heat the cell when in cold environments. In addition, there is a significant advantage to adding air flow on the anode side of the cell in a unique way.

An important application of this technology is for use in medical devices such as CPAP's. Positive airway pressure (PAP) is a mode of respiratory ventilation used primarily in the treatment of sleep apnea. PAP ventilation is also commonly used for those who are critically ill in hospital with respiratory failure, and in newborn infants (neonates). In these patients, PAP ventilation can prevent the need for tracheal intubation, or allow earlier extubating. Sometimes patients with neuromuscular diseases use this variety of ventilation as well. CPAP is an acronym for "continuous positive airway pressure", A continuous positive airway pressure (CPAP) machine was initially used mainly by patients for the treatment of sleep apnea at home, but now is in widespread use across intensive care units as a form of ventilation. Obstructive sleep apnea occurs when the upper airway becomes narrow as the muscles relax naturally during sleep. This reduces oxygen in the blood and causes arousal from sleep. The CPAP machine stops this phenomenon by delivering a stream of compressed air via a hose to a nasal pillow, nose mask, full-face mask, or hybrid, splinting the airway (keeping it open under air pressure) so that unobstructed breathing becomes possible, therefore reducing and/or preventing apneas and hypopneas. It is important to understand, however, that it is the air pressure, and not the movement of the air, that prevents the apneas. When the machine is turned on, but prior to the mask being placed on the head, a flow of air comes through the mask. After the mask is placed on the head, it is sealed to the face and the air stops flowing. At this point, it is only the air pressure that accomplishes the desired result. This has the additional benefit of reducing or eliminating the extremely loud snoring that sometimes accompanies sleep apnea.

The CPAP machine blows air at a prescribed pressure (also called the titrated pressure). The necessary pressure is usually determined by a sleep physician after review of a study supervised by a sleep technician during an overnight study (polysomnography) in a sleep laboratory. The titrated pressure is the pressure of air at which most (if not all) apneas and hypopneas have been prevented, and it is usually measured in centimeters of water (cmH2O). The pressure required by most patients with sleep apnea ranges between 6 and 14 cmH2O. A typical CPAP machine can deliver pressures between 4 and 20 cmH2O. More specialized units can deliver pressures up to 25 or 30 cmH2O.

CPAP treatment can be highly effective in treatment of obstructive sleep apnea. For some patients, the improvement in the quality of sleep and quality of life due to CPAP treatment will be noticed after a single night's use. Often, the patient's sleep partner also benefits from markedly improved sleep quality, due to the amelioration of the patient's loud snoring. Given that sleep apnea is a chronic health issue which commonly doesn't go away, ongoing care is usually needed to maintain CPAP therapy.

An automatic positive airway pressure device, APAP, AutoPAP, AutoCPAP, automatically titrates, or tunes, the amount of pressure delivered to the patient to the minimum required to maintain an unobstructed airway on a breath-by-breath basis by measuring the resistance in the patient's breathing, thereby giving the patient the precise pressure required at a given moment and avoiding the compromise of fixed pressure.

Bi-level positive airway pressure devices, BPAP, and variable positive airway pressure devices, VPAP, provide two levels of pressure: inspiratory positive airway pressure, IPAP, and a lower expiratory positive airway pressure, EPAP, for easier exhalation. Some people use the term BPAP to parallel the terms APAP and CPAP.) Often BPAP is incorrectly referred to as "BiPAP". However, BiPAP is the name of a portable ventilator manufactured by Respironics Corporation; it is just one of many ventilators that can deliver BPAP.

Expiratory positive airway pressure (Nasal EPAP) devices are used to treat primary snoring and obstructive sleep apnea (OSA). The device used to treat primary snoring is an over-the-counter version while the device for OSA is stronger and requires a prescription. OSA is a serious condition with significant consequences when left untreated. Snoring, while not as significant as OSA, still disturbs sleep and can cause potential harm, over time, to the sufferer. Devices in this category are relatively new and limited in number. Using the power of an individual's own breath, these devices don't require electricity to function. Typically, they fit over an individual's nostrils and contain a small valve which opens as you breathe in and closes as you breathe out, creating gentle pressure to naturally keep the airway open and relieve snoring.

There are many optional features generally increase the likelihood of PAP tolerance and compliance. One important feature is the use of a humidifier. Humidifiers add moisture to low humidity air which can increase patient comfort by eliminating the dryness of the compressed air. The temperature can usually be adjusted or turned off to act as a passive humidifier if desired. In general, a heated humidifier is either integrated into the unit or has a separate power source.

Mask liners: Cloth-based mask liners may be used to prevent excess air leakage and to reduce skin irritation and dermatitis.

An exemplary environment control system may be integrated with any of the PAP devices described herein and can increase oxygen as well as control humidity levels. In addition, an exemplary environment control device may be solid state and quiet, an important feature for a device utilized during sleep.

In an exemplary embodiment, a first electrochemical cell is configured to consume oxygen within an enclosure or flow stream and will therefore produce moisture in the enclosure or flow stream. A secondary control device, such as an ERV may be used to separately control the humidity levels. A second electrochemical cell may be coupled with the enclosure or flow stream and may be run in reverse of the first electrochemical cell to remove moisture from the enclosure or flow stream. In another embodiment, a layer of a moisture transmission membrane or material is configured over an opening to the enclosure and may draw humidity from the enclosure when there is a differential in humidity levels, RH, between the interior of the enclosure and exterior of the enclosure or flow conduit. A moisture transmission material may be pleated or corrugated to provide a higher surface area of the opening to the enclosure. An exemplary moisture transmission material is a ionomer, such as Nation® membrane, from E.I. DuPont, Inc, Wilmington, Delaware, or Gore-Select® membrane from W.L. Gore and Associates, Inc., Newark, Delaware. In still another embodiment, a dehumidifier may be configured with the enclosure or flow stream to remove excess moisture produced by the oxygen depleting electrochemical cell. This application incorporates by reference, in their entirety, U.S. provisional patent applications No. 62/353,545, filed on Jun. 22, 2016, application No. 62/258,945 filed on Nov. 23, 2015 and application No. 62/373,329 filed on Aug. 10, 2016.

This application incorporates by reference, in their entirety, the following: U.S. provisional patent application No. 62/171,331, filed on Jun. 5, 2015 and entitled Electrochemical Compressor Utilizing a Preheater; U.S. patent application Ser. No. 14/859,267, filed on Sep. 19, 2015, entitled Electrochemical Compressor Based Heating Element and Hybrid Hot Water Heater Employing Same; U.S. patent application Ser. No. 13/899,909 filed on May 22, 2013, entitled Electrochemical Compressor Based Heating Element And Hybrid Hot Water Heater Employing Same; U.S. provisional patent application No. 61/688,785 filed on May 22, 2012 and entitled Electrochemical Compressor Based Heat Pump For a Hybrid Hot Water Heater; U.S. patent application Ser. No. 14/303,335, filed on Jun. 12, 2014, entitled Electrochemical Compressor and Refrigeration System; U.S. patent application Ser. No. 12/626,416, filed on Nov. 25, 2009, entitled Electrochemical Compressor and Refrigeration System now U.S. Pat. No. 8,769,972; and U.S. provisional patent application No. 61/200,714, filed on Dec. 2, 2008 and entitled Electrochemical Compressor and Heat Pump System; the entirety of each related application is hereby incorporated by reference.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
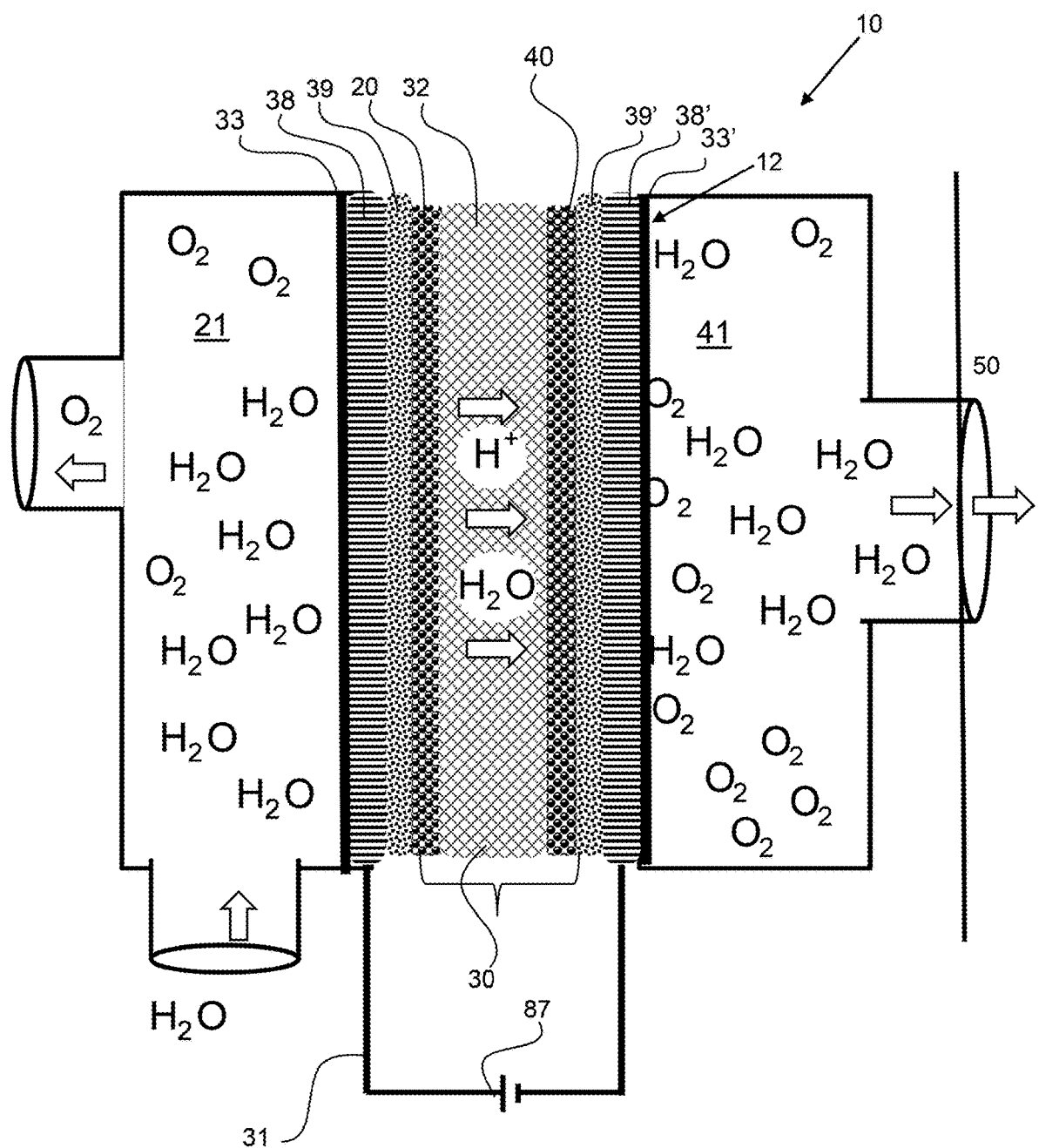

FIG. 1 shows an exemplary electrochemical cell comprising a membrane electrode assembly connected to a circuit for delivery of power from a power source, wherein electrolysis of water on the anode side produces protons that are transported across the ion conducting membrane to the cathode side.

Figure 2:
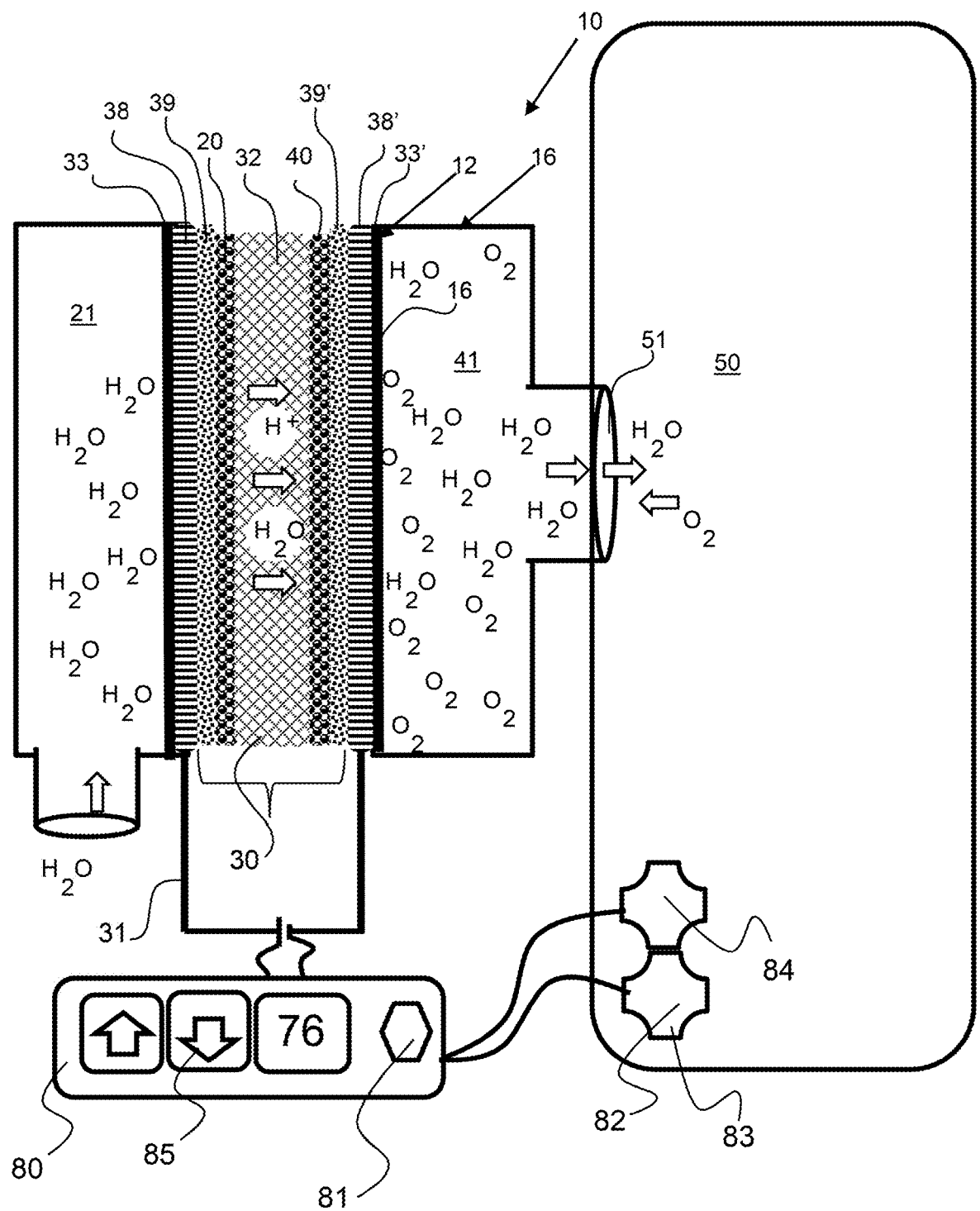

FIG. 2 shows an exemplary environment control system comprising an electrochemical cell coupled with an enclosure.

Figure 3:
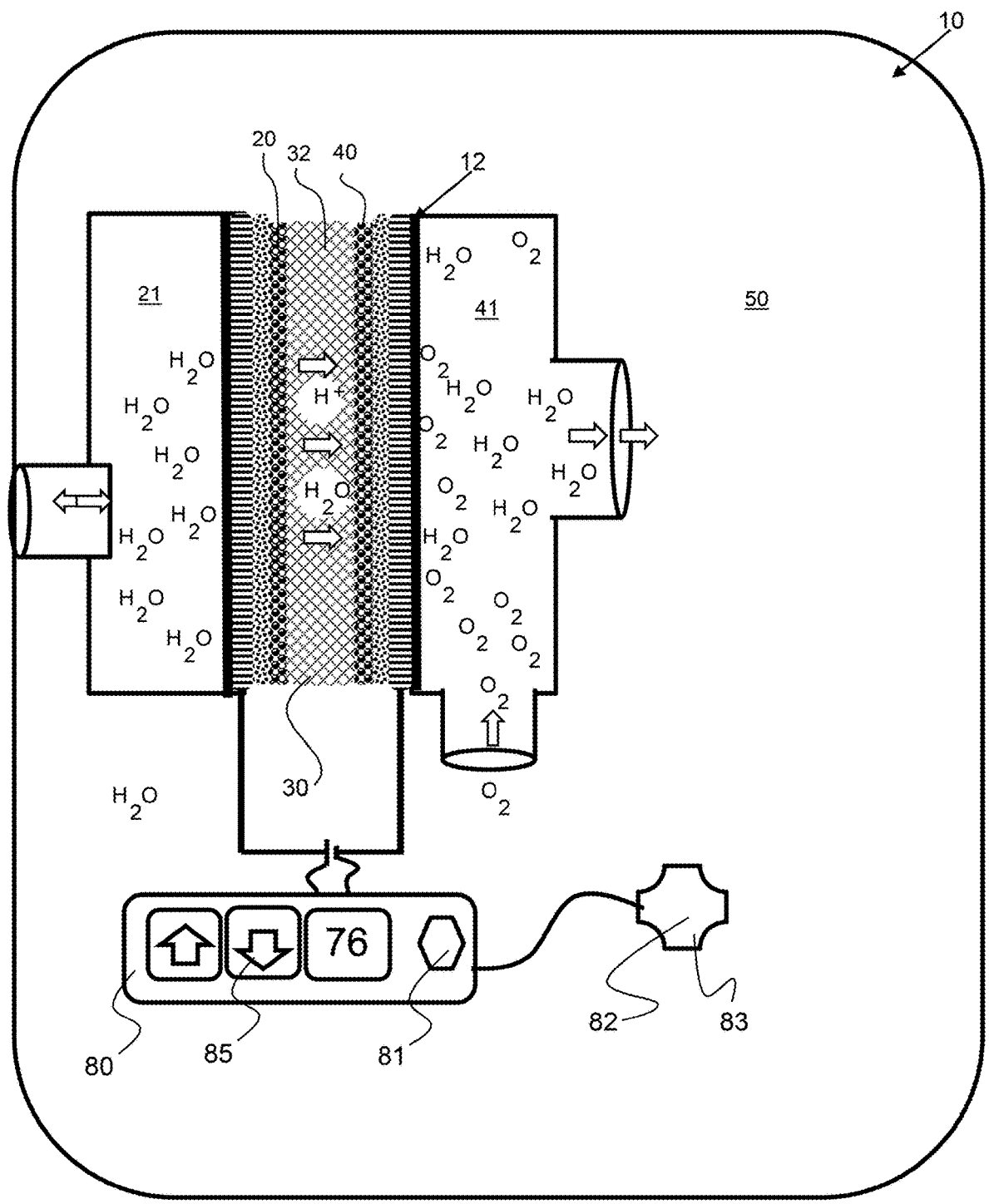

FIG. 3 shows an exemplary environment control system configured at least partially within an enclosure.

Figure 4:
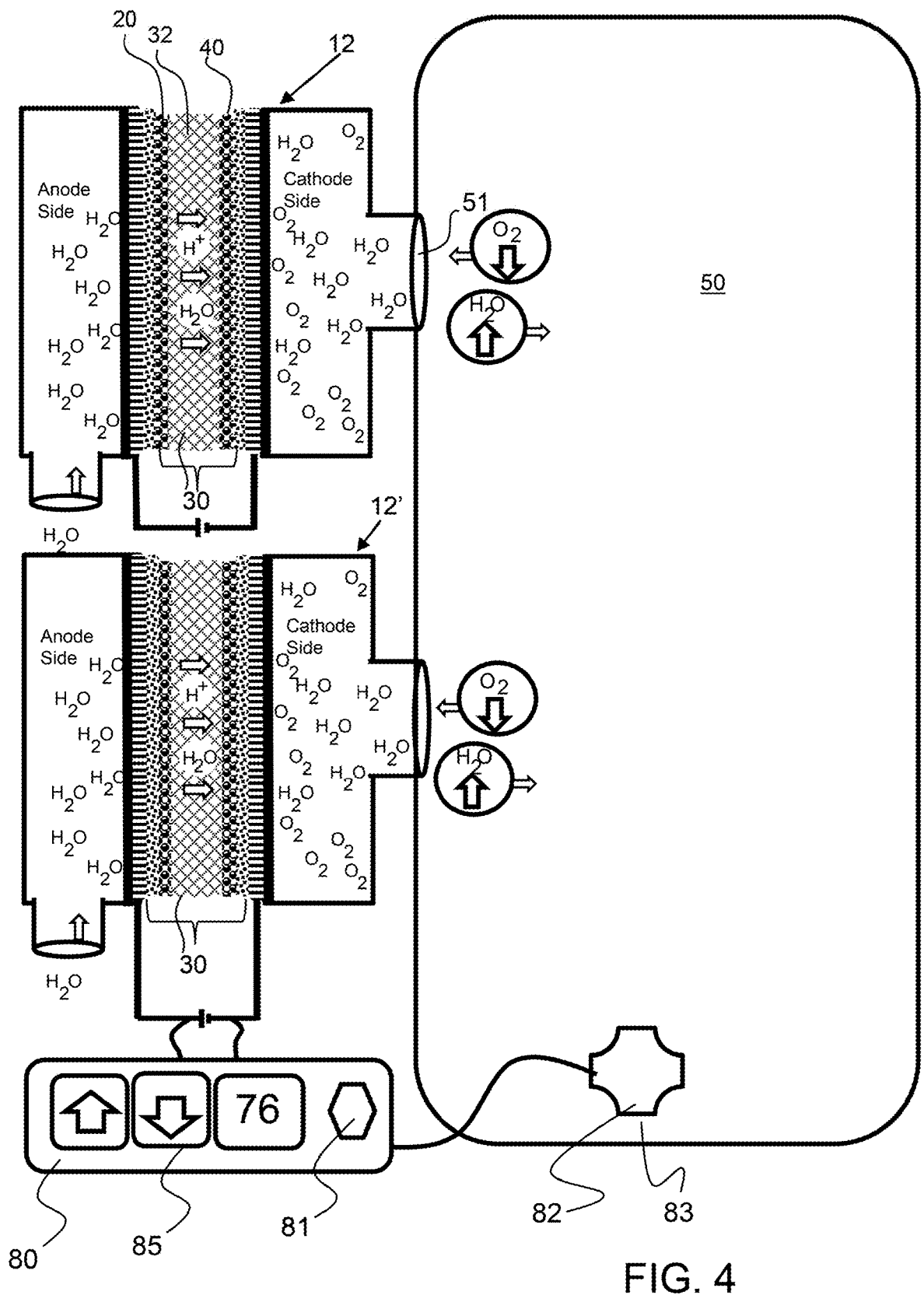

FIG. 4 shows an exemplary environment control system comprising two electrolyzer cells coupled with an enclosure.

Figure 5:
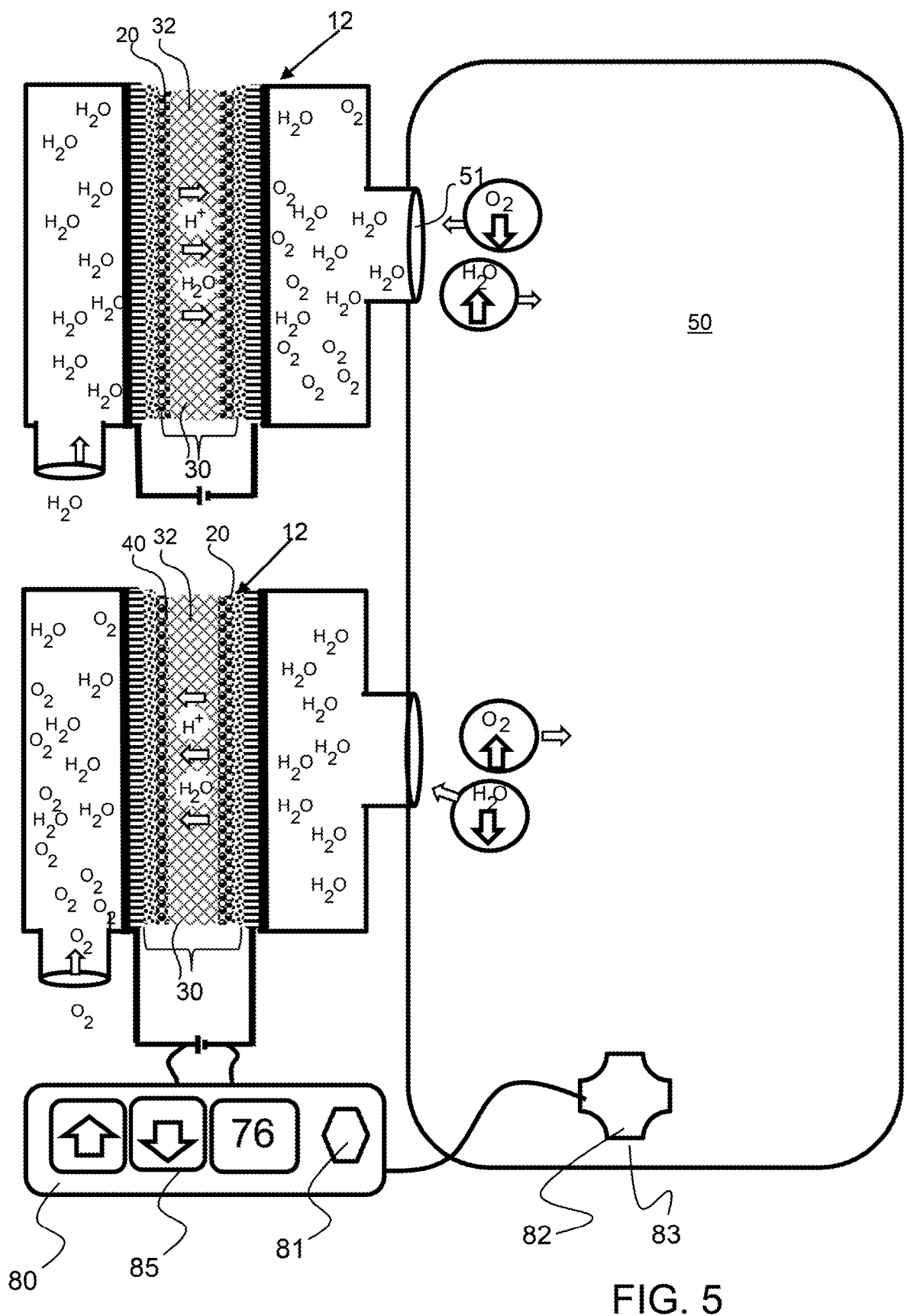

FIG. 5 shows an exemplary environment control system comprising two electrolyzer cells coupled with an enclosure with one of the cells having the anode in fluid communication with the enclosure and the other cell having the cathode in fluid communication with the enclosure.

Figure 6:
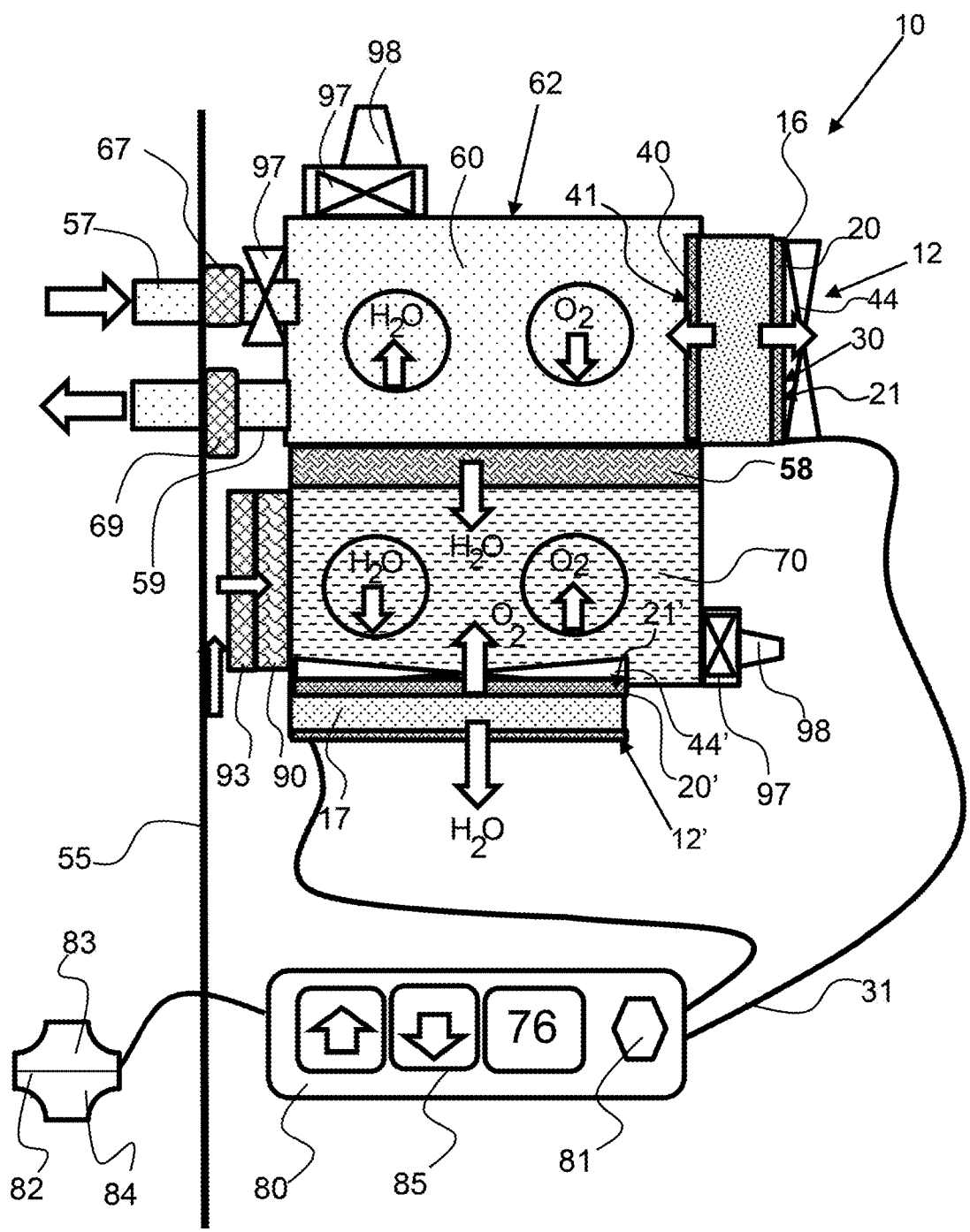

FIG. 6 shows a diagram of an exemplary environment control system having a separator to draw moisture from the oxygen control chamber.

Figure 7:
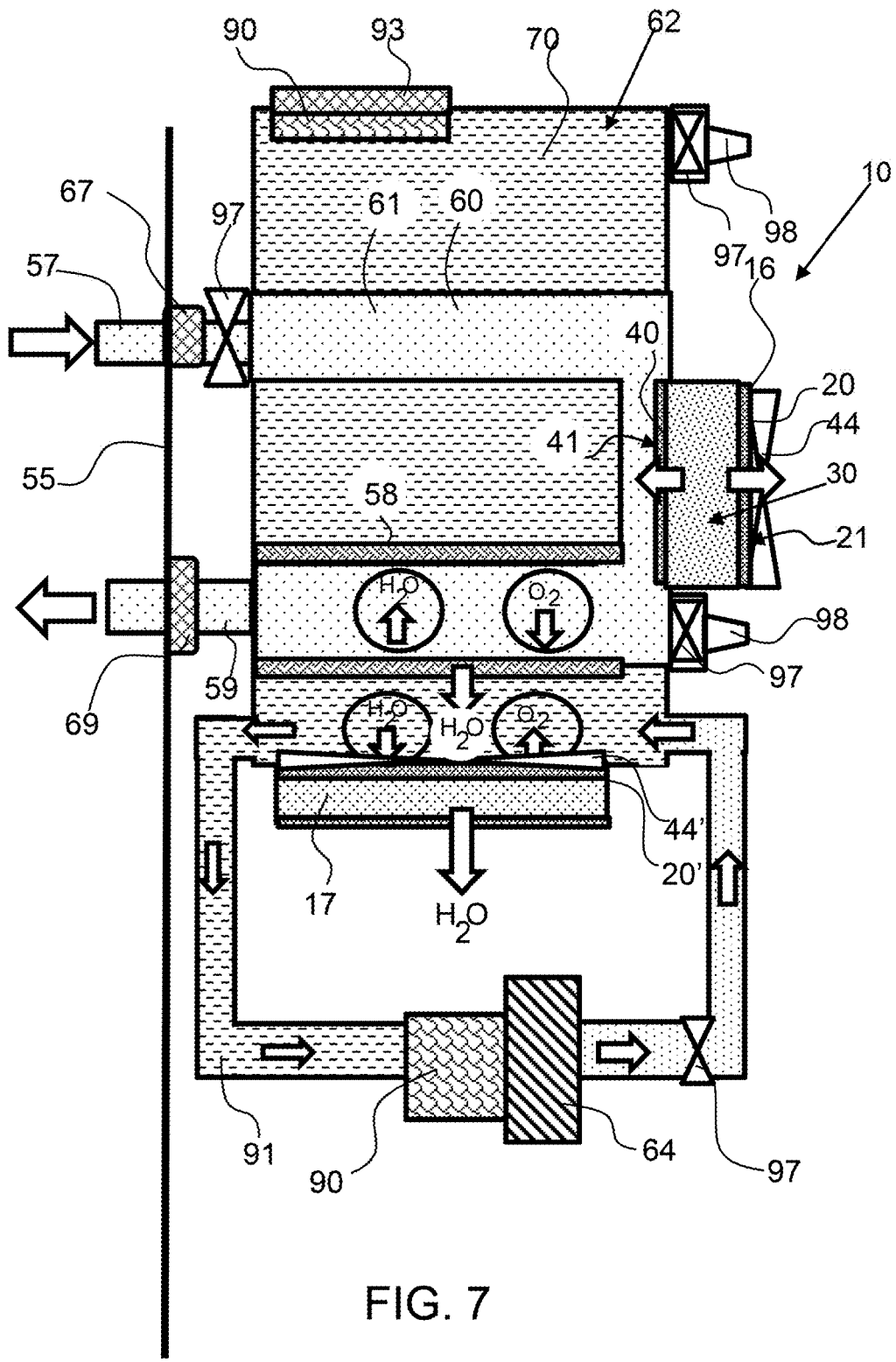

FIG. 7 shows a diagram of an exemplary environment control system having an exchange conduit through the conditioner chamber that exchanges moisture through a separator.

Figure 8:
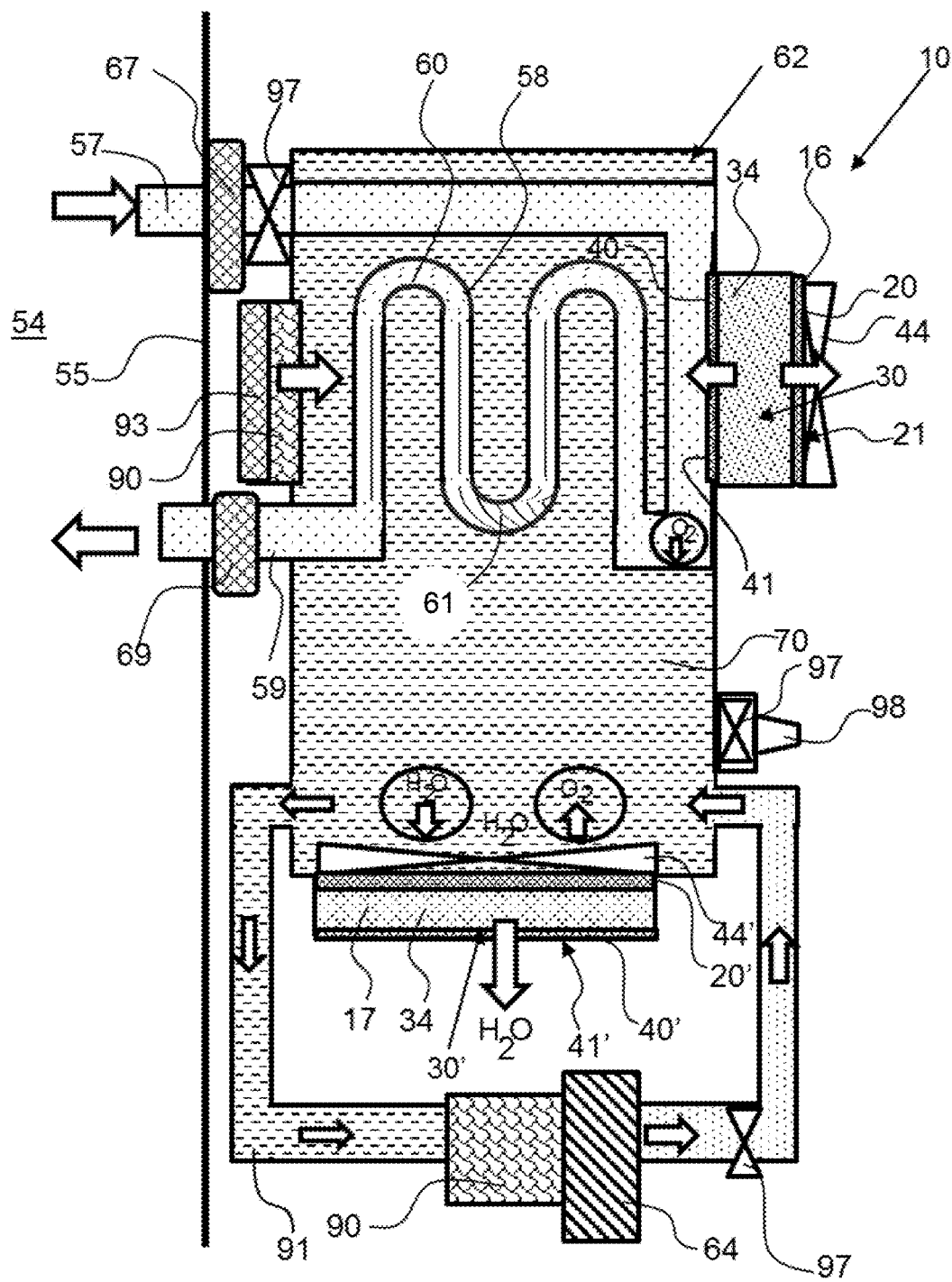

FIG. 8 shows a diagram of an exemplary environment control system having a serpentine exchange conduit through the conditioner chamber to enable effective moisture transfer from the exchange conduit to the conditioner chamber.

Figure 9:
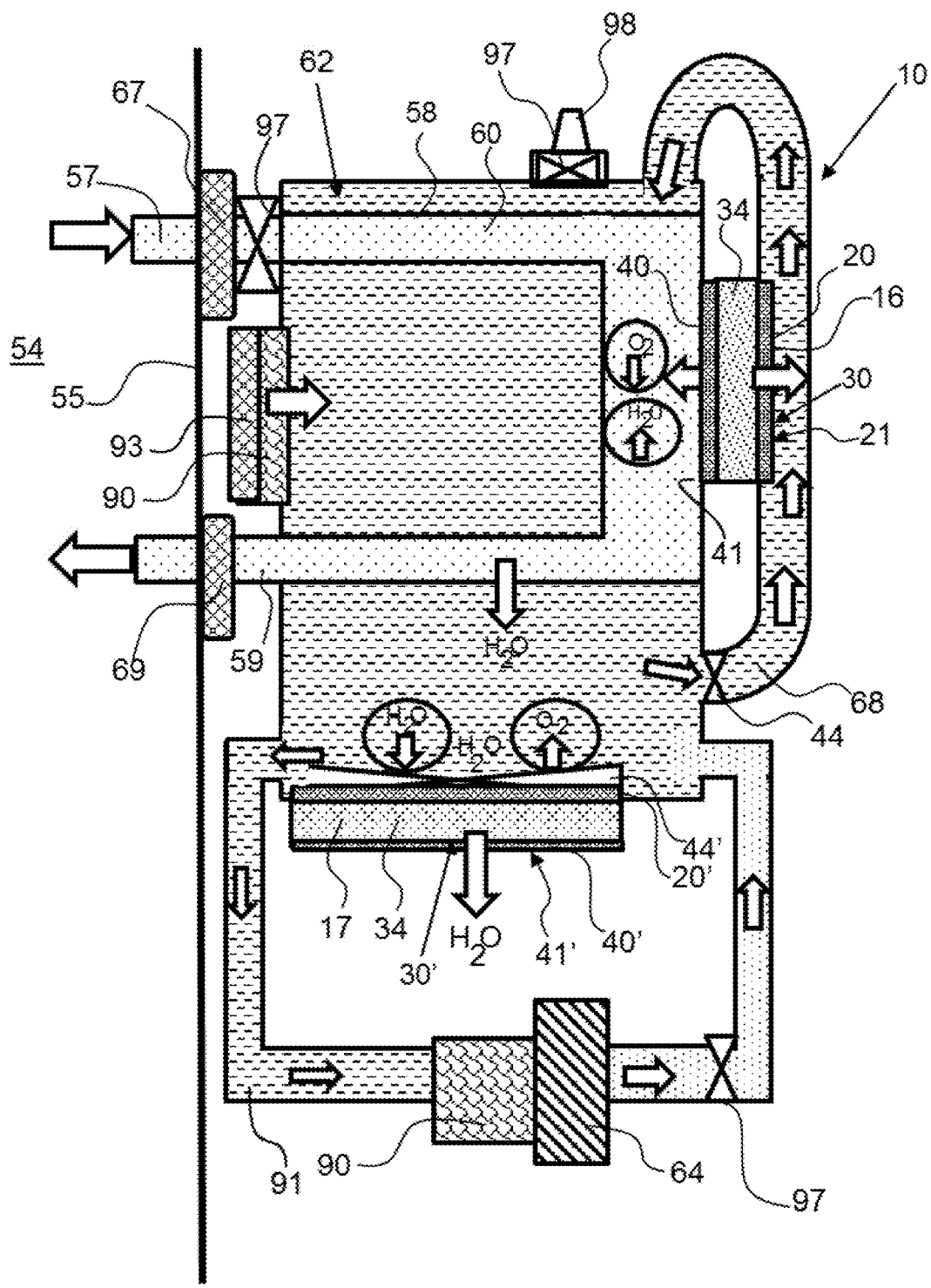

FIG. 9 shows a diagram of an exemplary environment control system having a recirculation loop between the conditioner chamber and the anode side of oxygen depletion electrolyzer cell.

Figure 10:
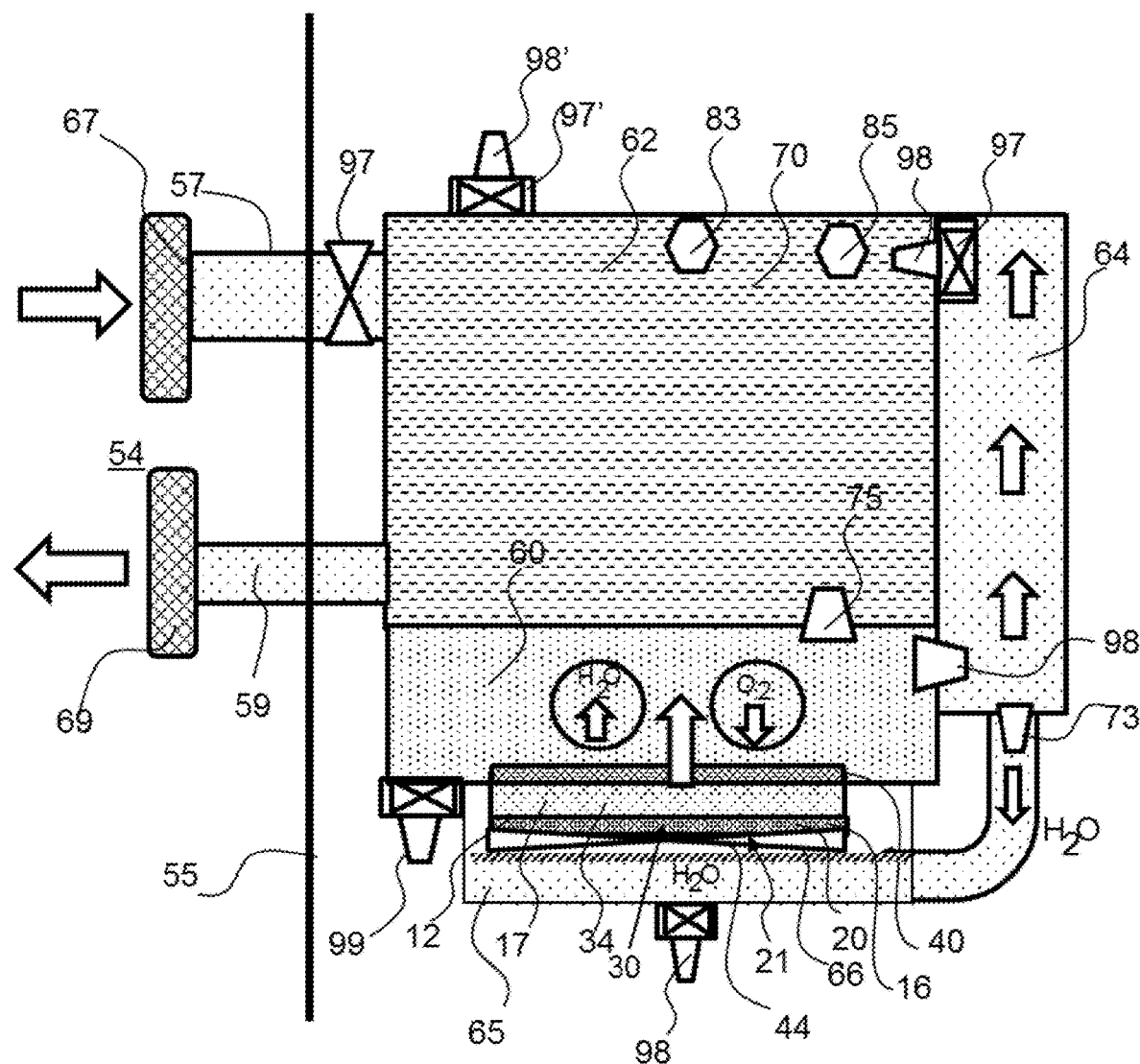

FIG. 10 shows a diagram of an exemplary environment control system having a water chamber and an oxygen bleed valve.

Figure 11:
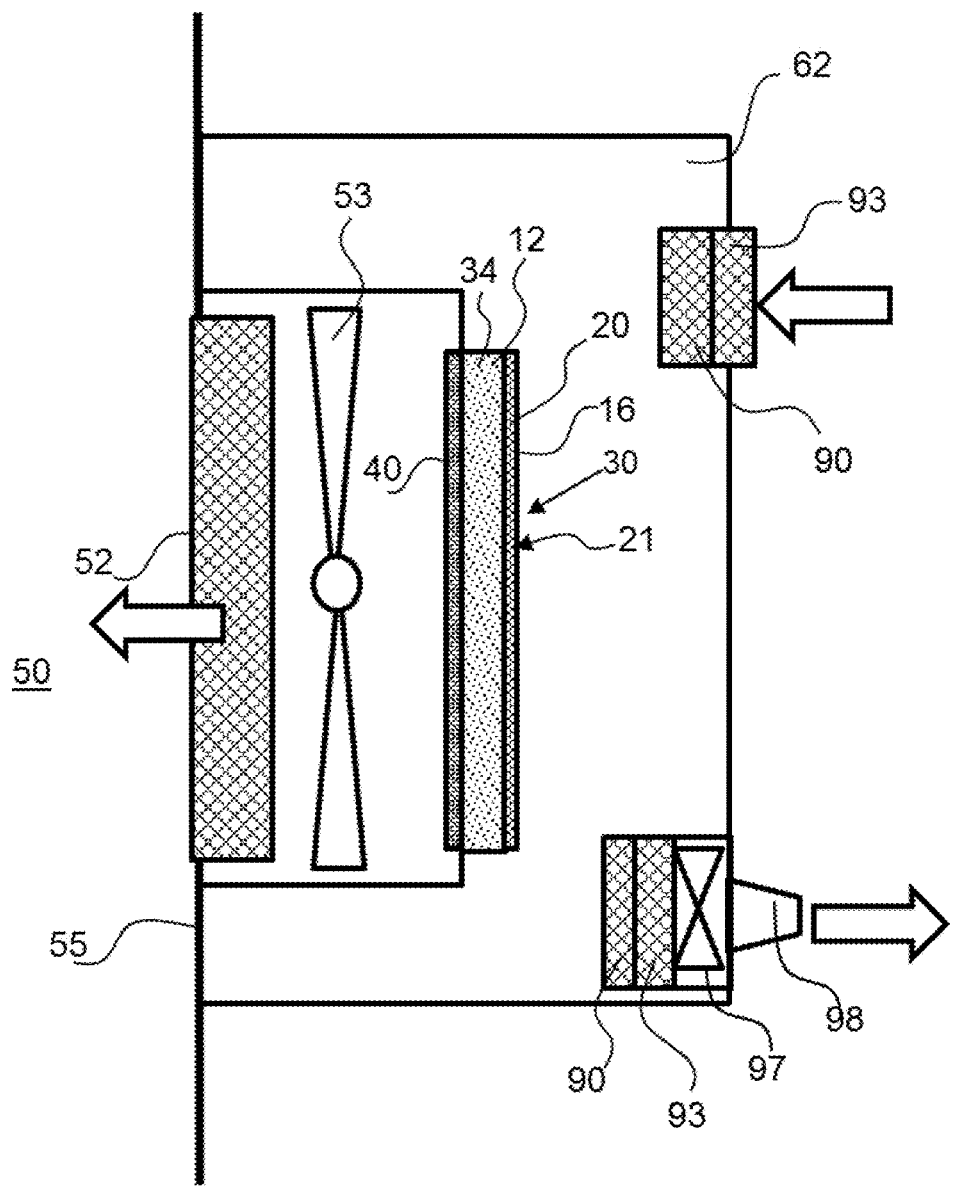

FIG. 11 shows a diagram of an exemplary environment control system having an enclosure filter, a conditioner chamber and inlet and outlet filters to the conditioner chamber.

Figure 12:
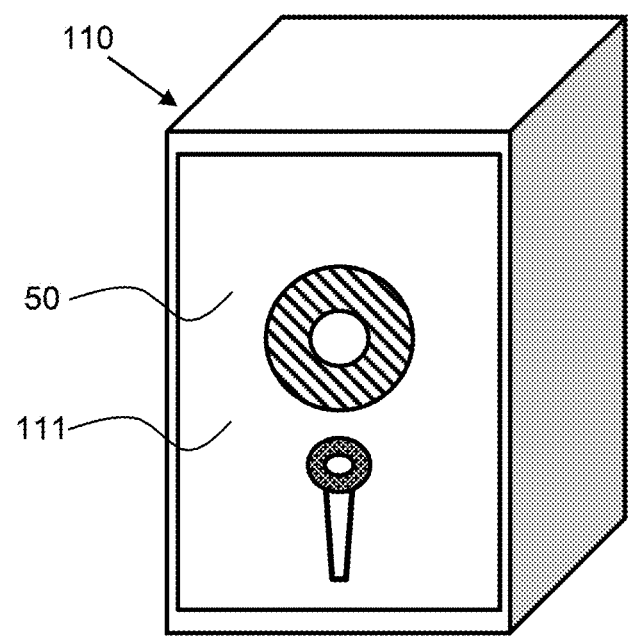

FIG. 12 shows a front view of a safe having a lock on the front door.

Figure 13:
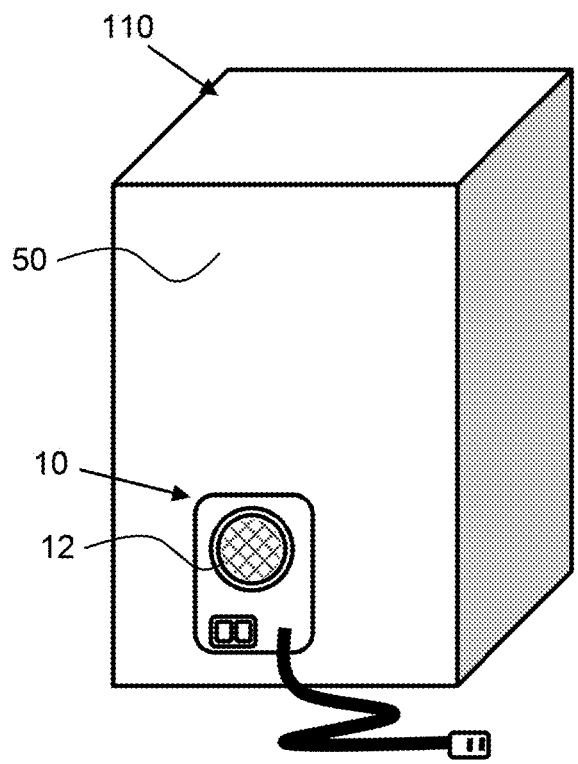

FIG. 13 shows a back view of the safe shown in FIG. 12 with an exemplary environment control system coupled to the back.

Figure 14:
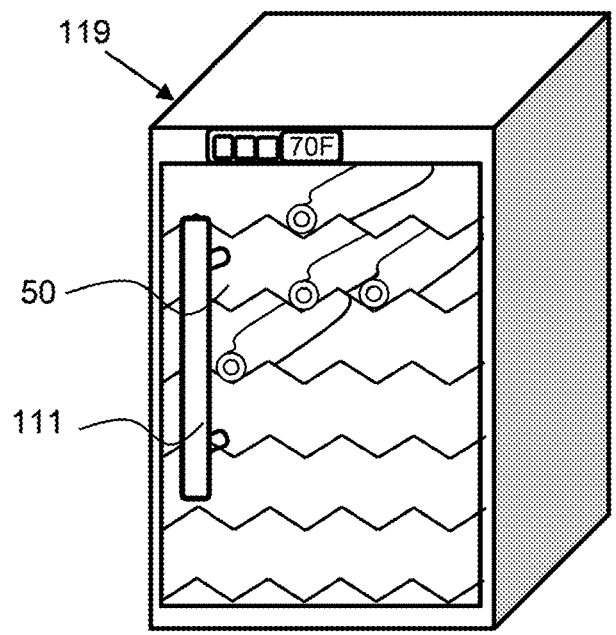

FIG. 14 shows a front view of a wine cooler having a front door to the interior of the enclosure.

Figure 15:
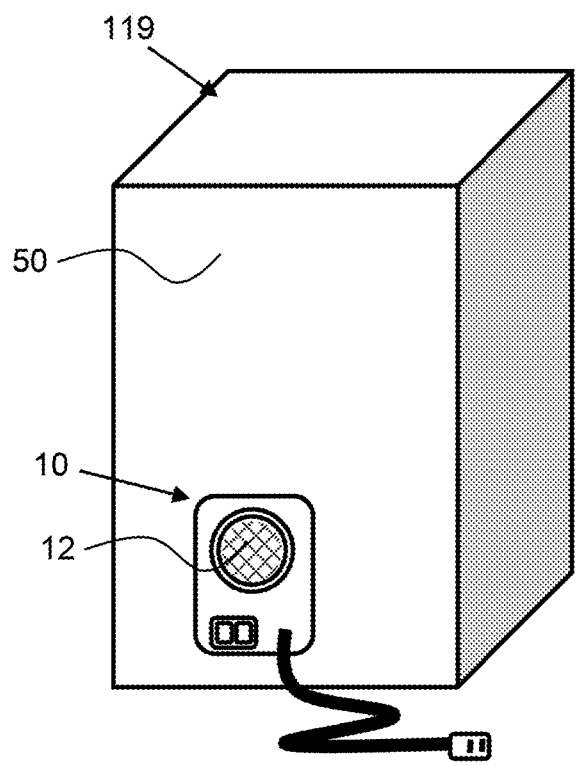

FIG. 15 shows a back view of the wine cooler shown in FIG. 14 with an exemplary environment control system coupled to the back.

Figure 16:
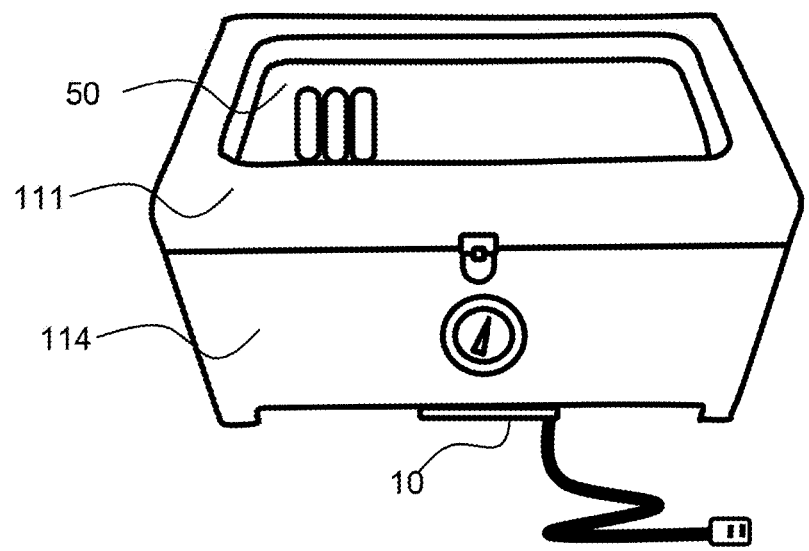

FIG. 16 shows a front perspective view of a humidor having a door to the interior of the enclosure on the top.

Figure 17:
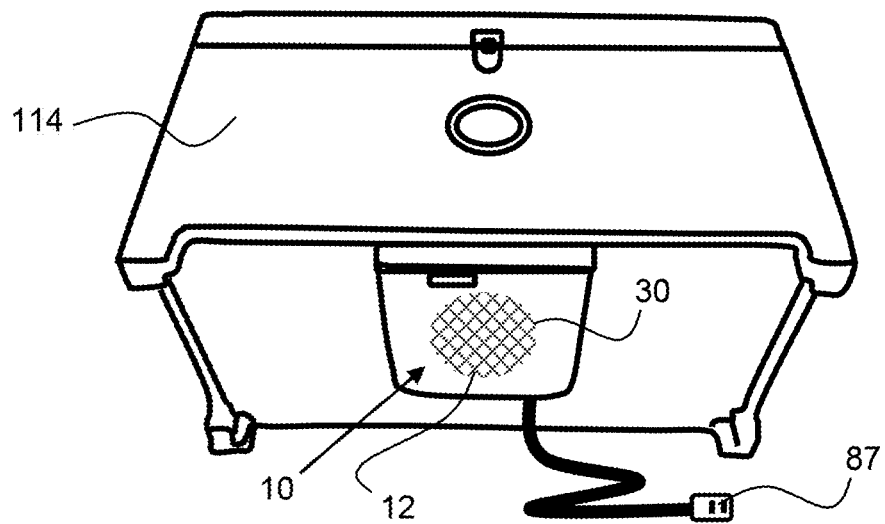

FIG. 17 shows a bottom perspective view of the humidor shown in FIG. 16 with an exemplary environment control system coupled to the bottom.

FIG. 16 shows a bottom perspective view of the humidor shown in FIG. 15 with an exemplary environment control system coupled to the bottom.

Figure 18:
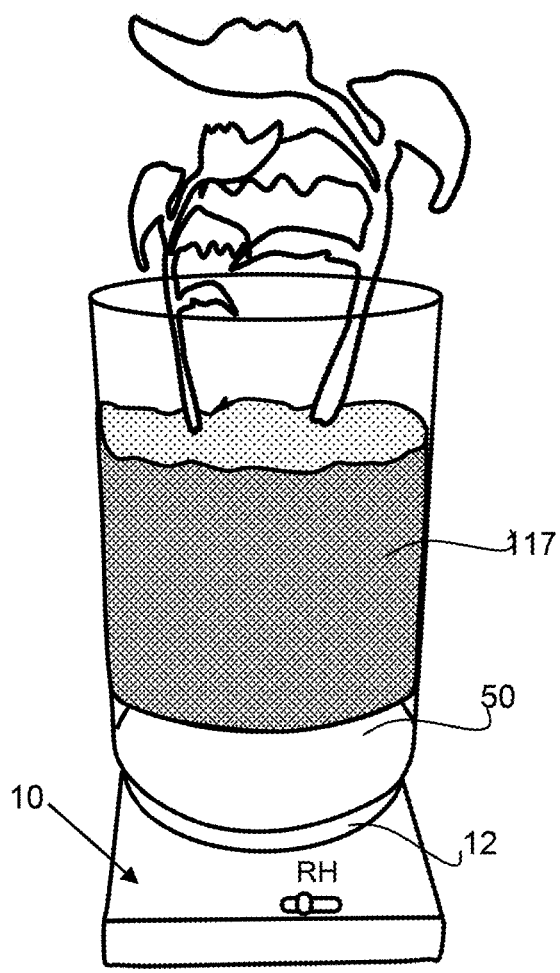

FIG. 18 shows a side view of an exemplary environment control system configured to control the environment of growing enclosure, such as a vase or pot for growing a plant.

Figure 19:
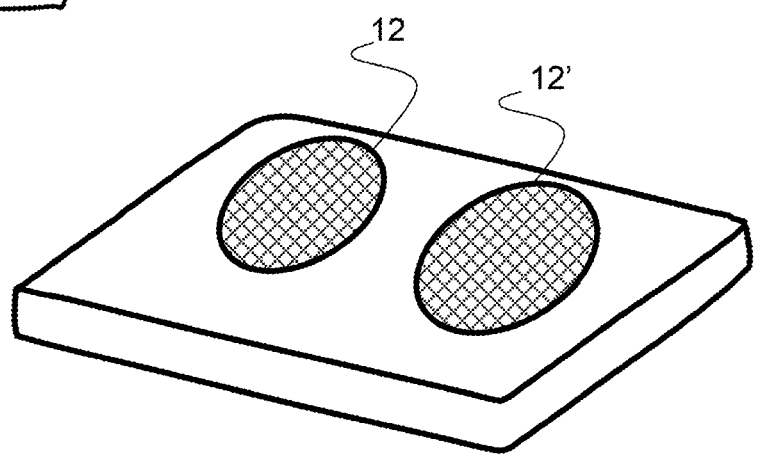

FIG. 19 shows a perspective vie of an exemplary environment control system having two electrolyzer cells for placement of an enclosure thereon.

Figure 20:
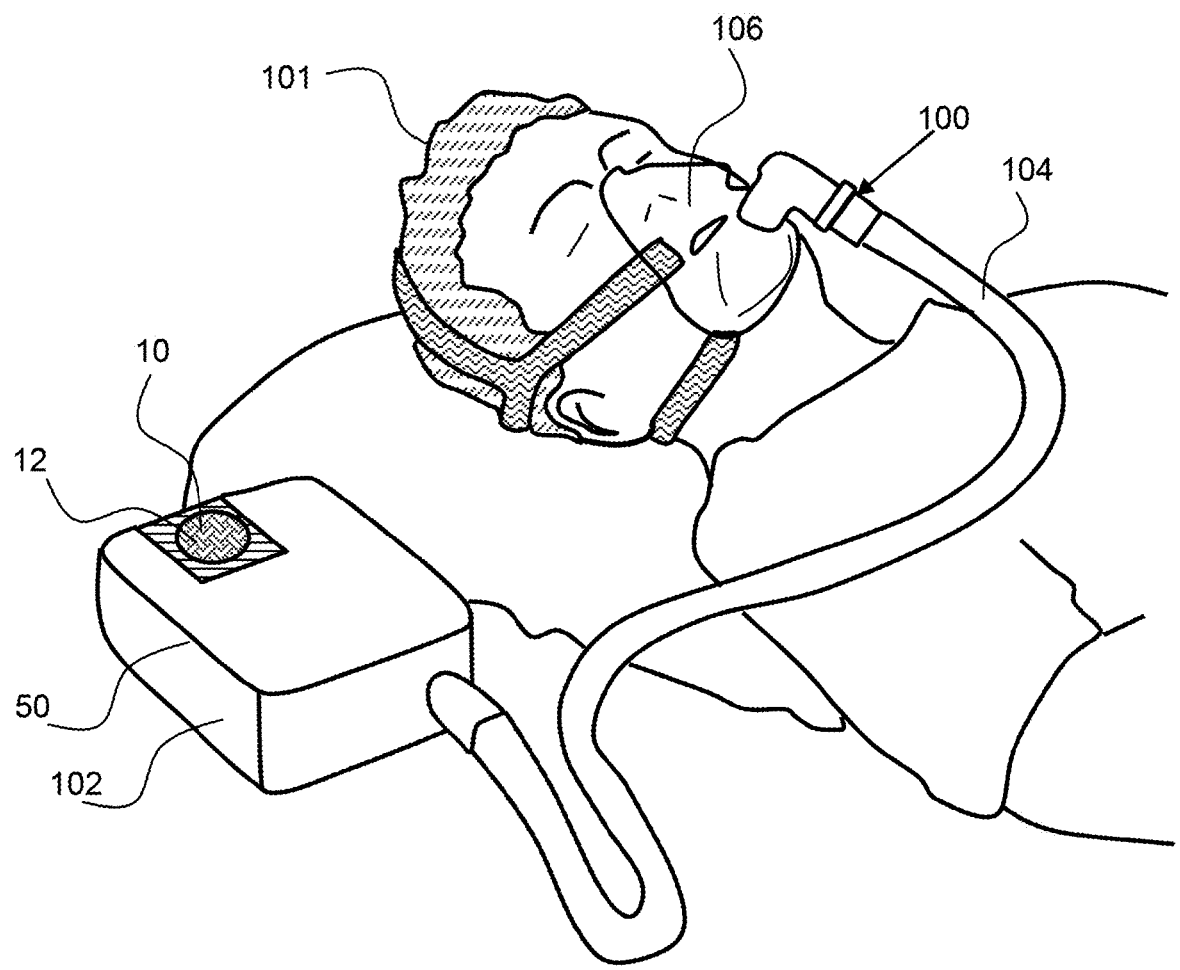

FIG. 20 shows a person sleeping with the aid of a Positive Airway Pressure, PAP, device having an exemplary environment control system.

Figure 21:
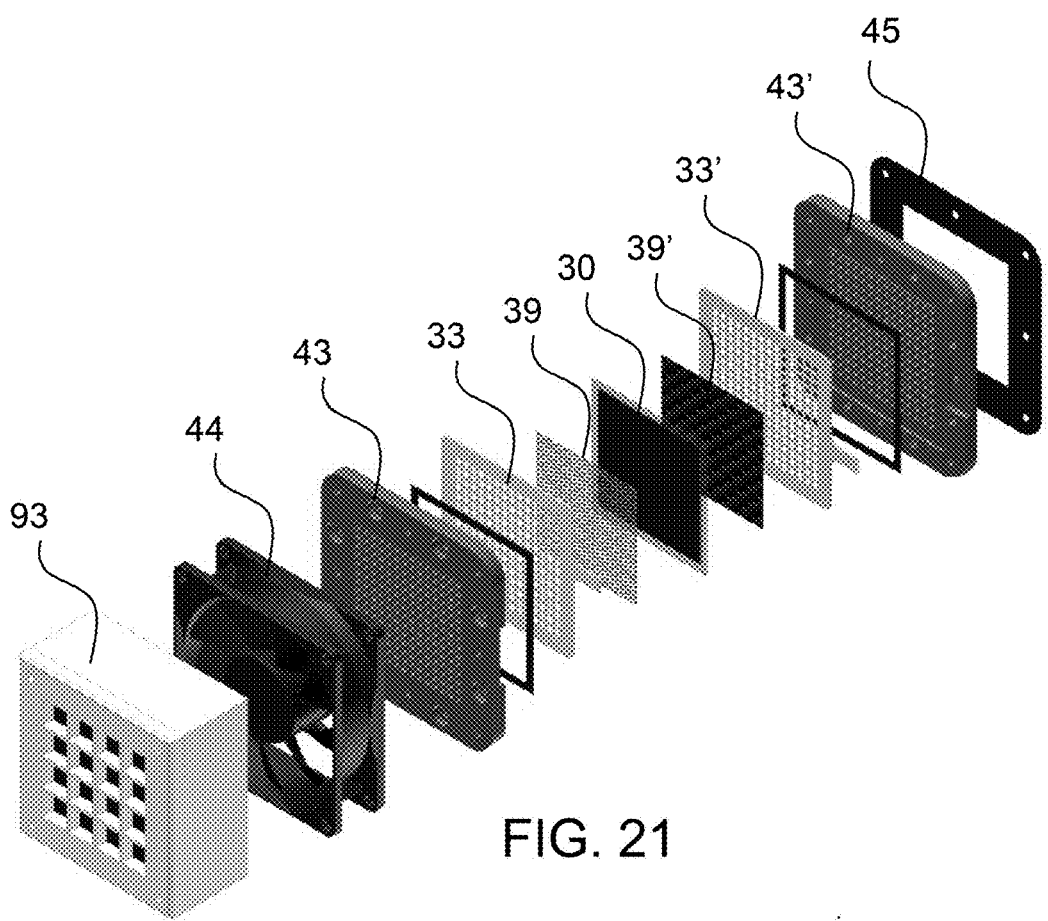

FIG. 21 shows a perspective exploded view of an exemplary electrolyzer cell.

Figure 22:
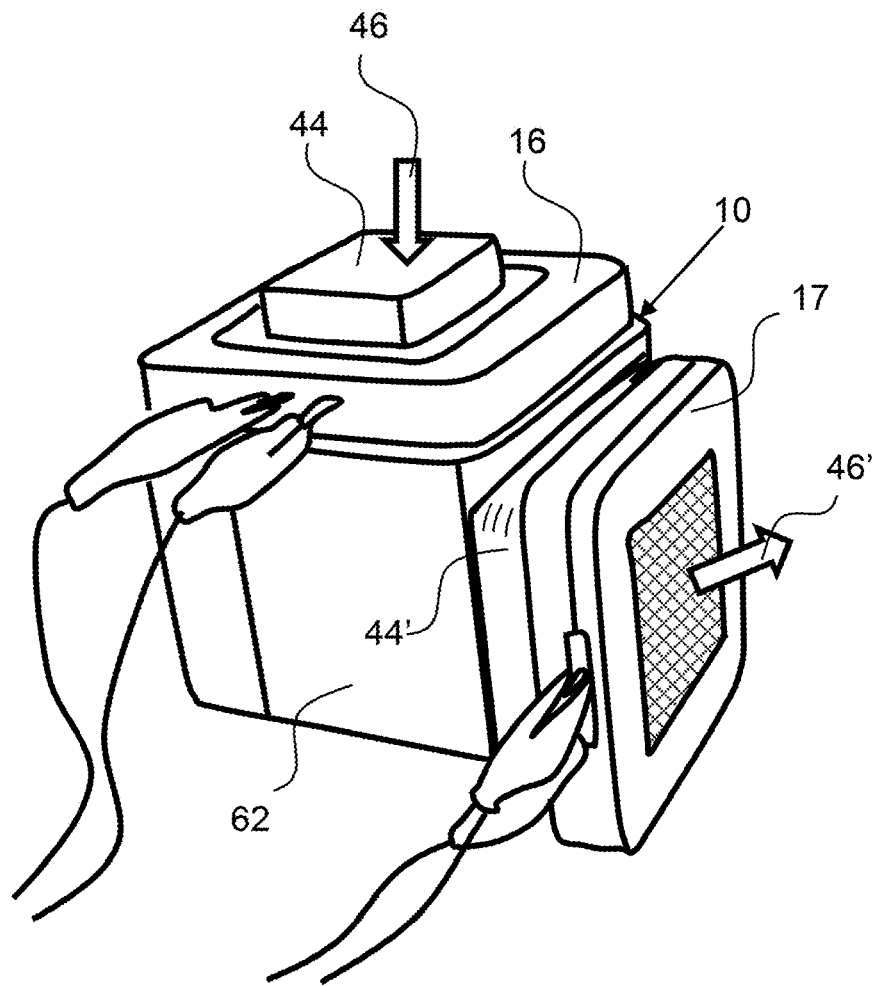

FIG. 22 shows a perspective view of an exemplary environment control device.

Figure 23:
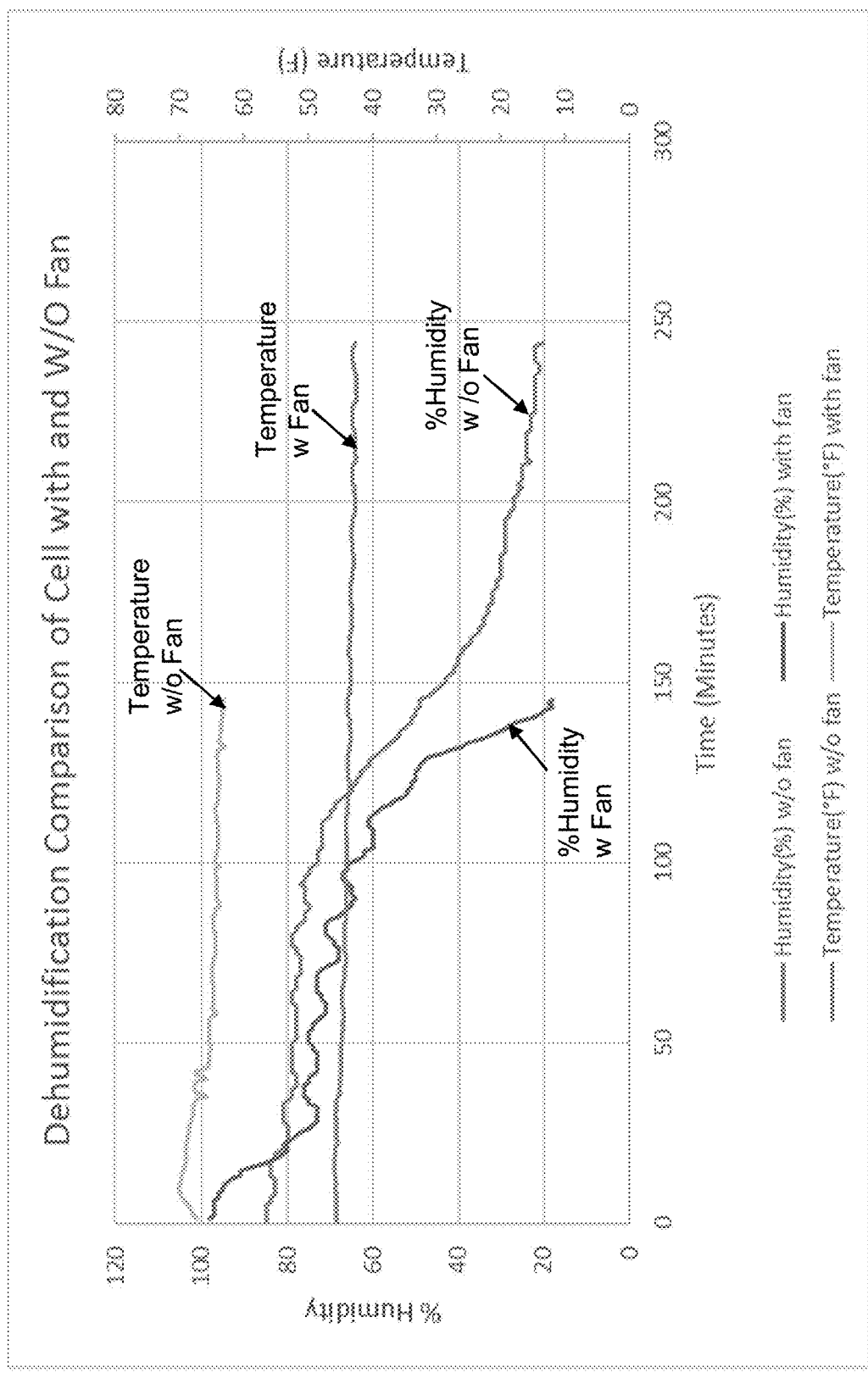

FIG. 23 shows a graph of an enclosure temperature and humidity with and without a fan blowing onto the cathode of a humidity control electrolyzer.

Figure 24:
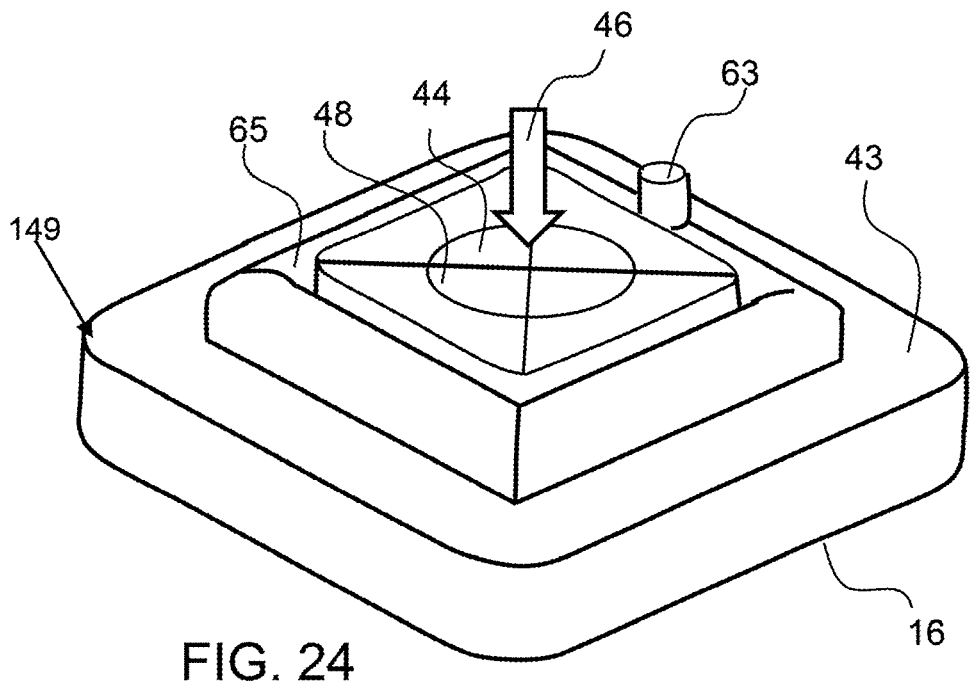
Figure 25:
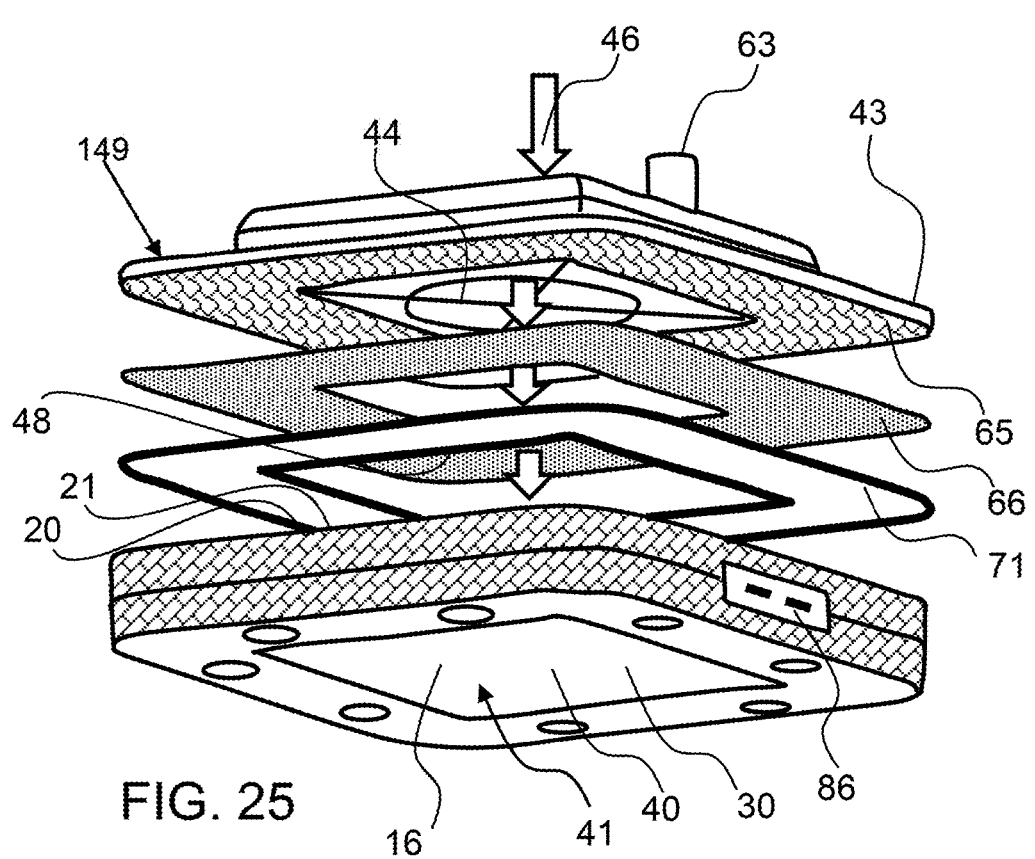

FIGS. 24 and 25 show a perspective view of an exemplary oxygen control electrolyzer cell configured with an MEA air moving device to produce a flow of process the anode of the membrane electrode assembly.

Figure 26:
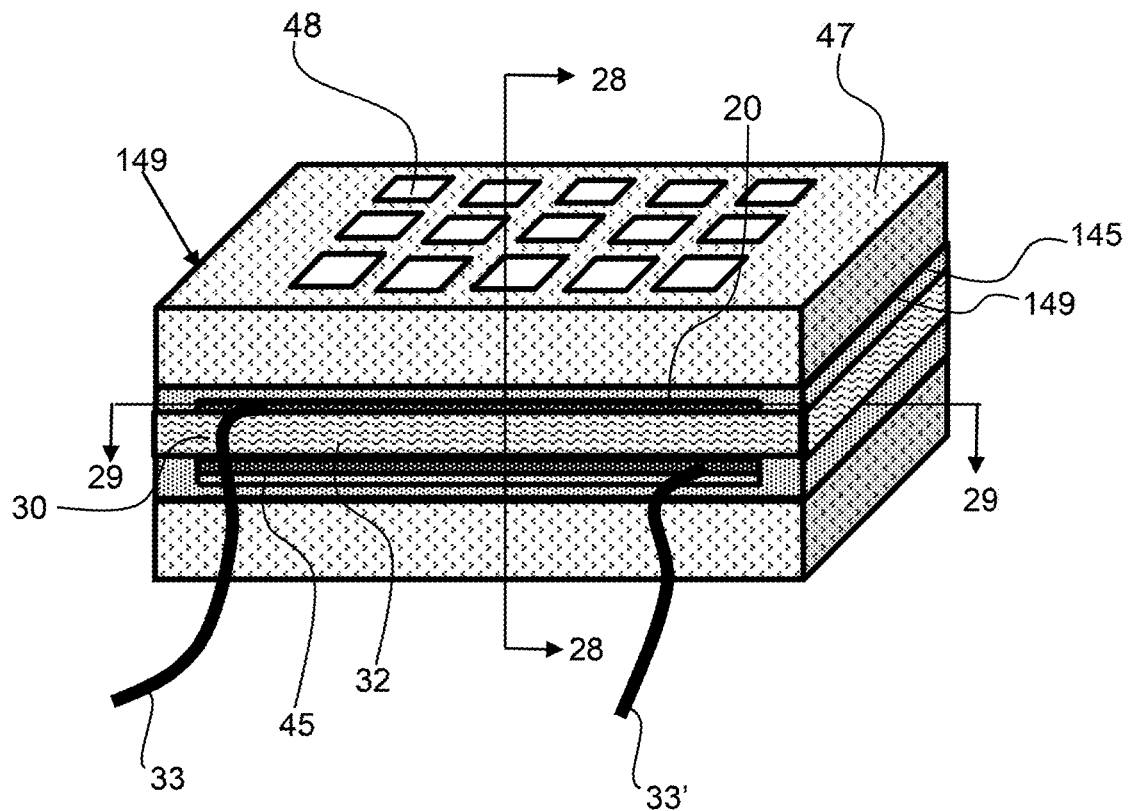

FIG. 26 shows a perspective view of a membrane electrode assembly attached to a housing.

Figure 27:
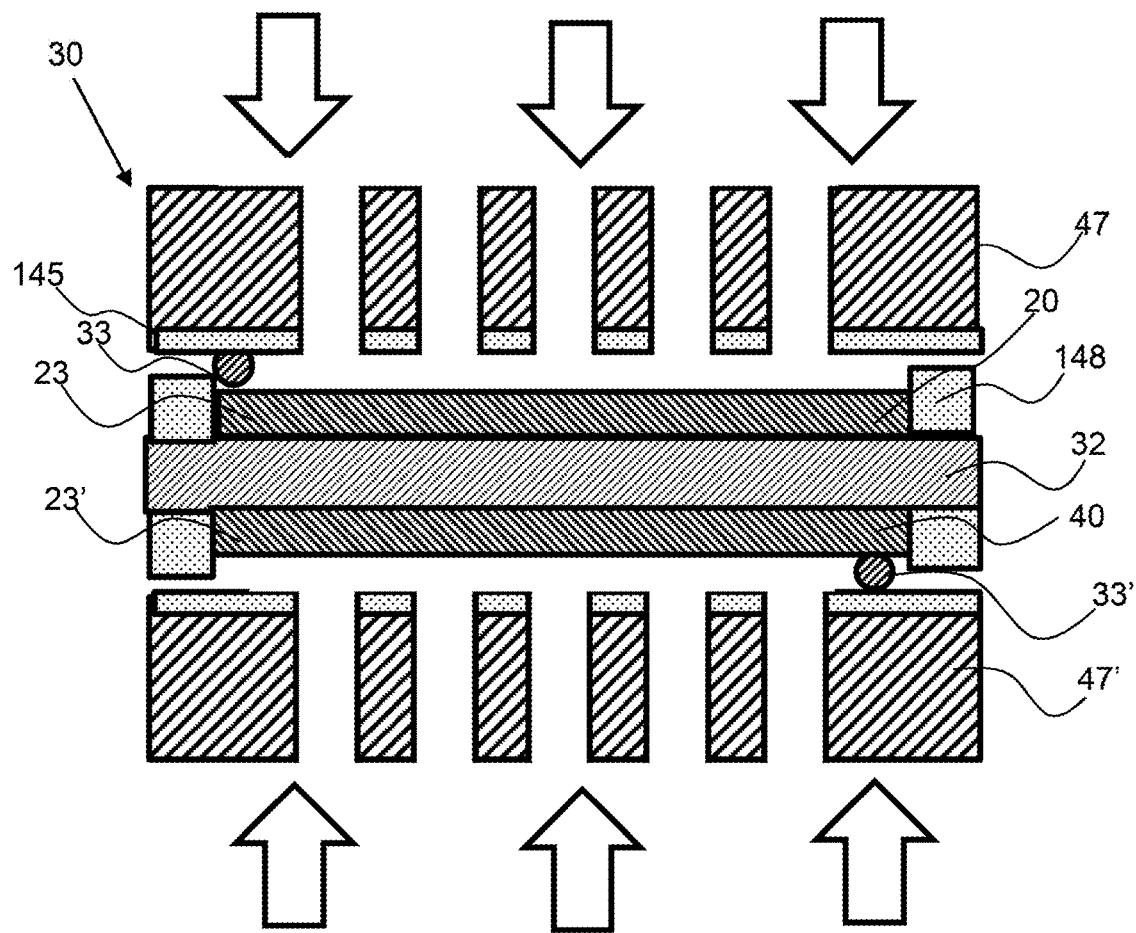

FIG. 27 shows a cross-sectional view of a membrane electrode assembly being attached to a housing.

Figure 28:
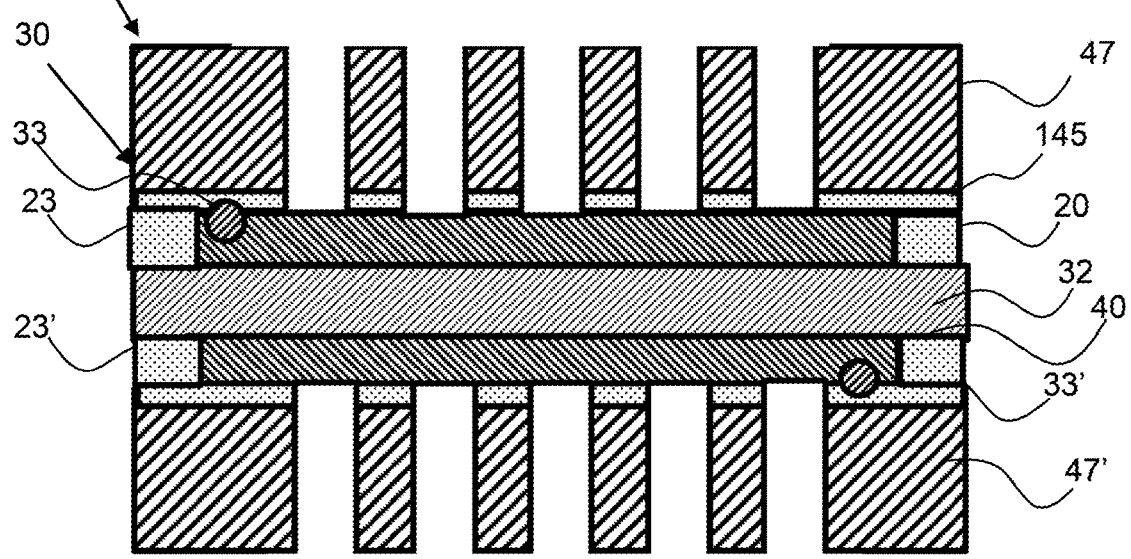

FIG. 28 shows a cross-sectional view of the membrane electrode assembly of FIG. 26 along line 28.

Figure 29:
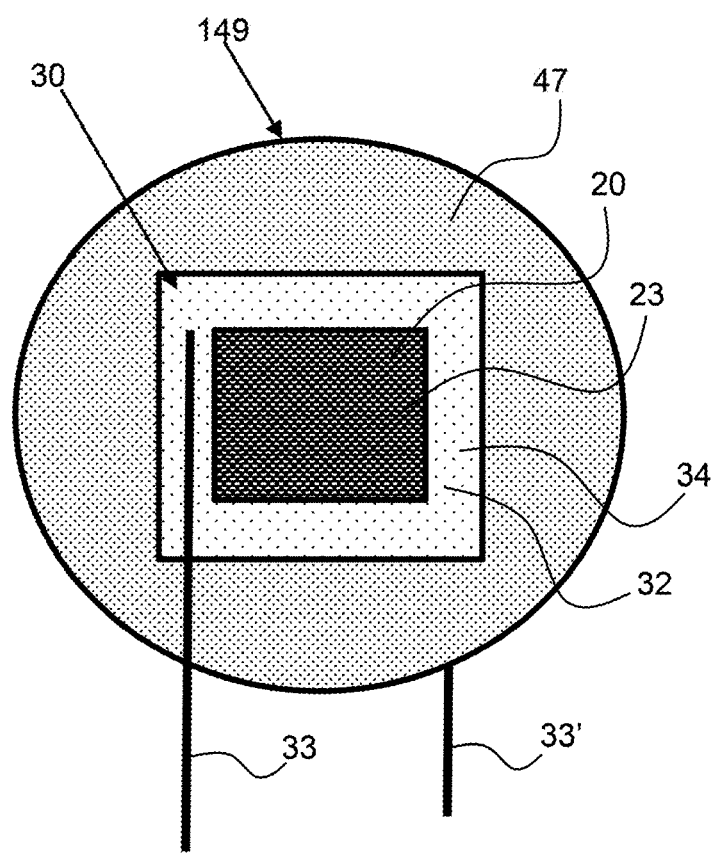

FIG. 29 shows a cross-sectional view of the membrane electrode assembly of FIG. 26 along line 29.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

An integral membrane electrode assembly is a membrane electrode assembly bonded, by an adhesive, to an integral housing. A housing may be rigid such as a plastic frame, or may be a flexible and pliable, such as a fabric, wherein the integral membrane electrode assembly can be folded without damage to the integral MEA. An exemplary housing has openings to allow air to flow to the anode on the anode side and air to flow the cathode from the cathode side. Note that the anode and cathode are separated by a substantially air impermeable layer, such as the ionomer layer or a separate gasket layer that prevents air from the anode from passing over to the cathode side and vice versa. A gasket may extend around the anode and cathode area and provide a perimeter for attaching the housing or for attaching the integral membrane electrode assembly to an enclosure, such as over an opening to the enclosure.

FIG. 1 shows an exemplary environment control system 10 that utilizes an electrochemical cell 12 comprising a membrane electrode assembly 30 connected to a circuit 31 for delivery of power from a power source 87. The anode 20 of the MEA reacts with water to produce oxygen and protons. The protons $H^+$ pass through proton conducting layer such as an ionomer, an example of an ion exchange medium 32, to the cathode 40. Water is pulled through the ionomer along with the protons. At the cathode, the protons react with oxygen and produce water, thereby reducing the oxygen at the cathode and increasing water. The cathode is in fluid communication with the enclosure 50 and therefore reduces the oxygen concentration and increases the moisture or RH of the enclosure. The electrochemical cell also includes gas diffusion layers 39,39', flow fields 38, 38' and current collectors 33, 33' configured on the anode and cathode, respectively.

As shown in FIG. 2, an exemplary electrochemical cell 12 utilizes a, membrane electrode assembly, MEA 12, connected to a circuit 31 for power. As shown, this is an oxygen control electrolyzer cell 16 that is reducing oxygen concentration in the enclosure 50. An electrical potential is created across the anode and cathode to initiate the electrolysis of water on the anode 20, that produces oxygen and protons that are transported across the ion conducting media 32 or membrane, or ionomer, to the cathode 40. A chamber is configured on the anode side 21 for receiving incoming air and water moisture and a chamber or space on the cathode side 41 is in fluid communication with an enclosure 50, such as through one or more openings 51 into the enclosure. On the cathode, the protons are reacted with oxygen to produce water. Oxygen is depleted on the cathode side and water is produced. The protons also drag water across the ionomer from the anode side to the cathode side. On the anode side, oxygen is produced and water is consumed in electrolysis reaction that produces oxygen and protons. The membrane electrode assembly is coupled between two electrical current collectors 33, or electrically conductive layers, that provide the electrical power to the MEA. An electrical conductor plate, may be a screen or perforated metal and may be the gas diffusion media and/or a flow field. A flow field 38 may have a plurality of channels for distributing gasses to the surface of the MEA or gas diffusion media. A gas diffusion media 39 may further distribute gas to the anode and cathode. A sensor 82, such as a humidity sensor 83 and/or oxygen sensor 84, may be coupled with a control system 80 for maintaining the humidity and/or oxygen level within the enclosure to a desired level. A user input 85 may be used to set a desired level or range of humidity and/or oxygen concentration within the enclosure and a micro-processor 81 may control the power supply to the electrochemical cell to keep the oxygen and humidity within the set points by the user. The electrochemical cell may be run in the opposite direction, wherein the anode is in fluid communication with the enclosure and reduces moisture and increase oxygen concentration.

As shown in FIG. 3, an exemplary environment control system 10 comprises an electrochemical cell 12 at least partially configured within the enclosure 50. As shown, this is an oxygen control electrolyzer cell 16 that is reducing oxygen concentration in the enclosure 50. In this embodiment, the MEA 30 may be run in a direction to produce moisture within the enclosure or to pump moisture out of the enclosure. An inlet/outlet conduit 25 on the anode side 21 extends out of the enclosure. Again, the electrochemical cell may be run to increase or decrease the humidity and/or oxygen concentration within the enclosure. The cell can be operated to pump water into the enclosure or operated to pump water out of the enclosure by changing the polarity across the anode and cathode. The humidification control system may provide humid air to the enclosure by control of the circuit power to drive the electrolysis of water. A sensor 82, such as a humidity sensor 83, monitors humidity and relays this measured value to the controller system 80. A processor 81 may control the amount of power, voltage and/or current to the MEA to control the amount of humid air provided to the enclosure. A user interface 85, as shown by the up and down arrows may be used to adjust the humidity level within the enclosure. The cathode side of the electrochemical cell is coupled with and enclosure and will reduce the oxygen level, while increasing the humidity level.

Referring now to FIGS. 4 and 5, an exemplary environment control system 10 comprises two electrochemical cells 12, 12' in fluid communication with the enclosure 50. The two cells may be operated in the same mode, such as oxygen depletion and humidification mode, as shown in FIG. 4, wherein the cathode is in fluid communication with the enclosure, thereby increase the rate of oxygen reduction within the enclosure and humidity increase within the enclosure. The two cells may also be operated in an oxygen increase and humidity reduction mode, wherein the anode is in fluid communication with the enclosure, thereby increasing the rate of oxygen increase and humidity reduction within the enclosure. Furthermore, the two electrochemical cells, may be operated in opposing modes, as shown in FIG. 5, wherein one electrochemical cell is configured to reduce oxygen concentration within the enclosure and one is configured to increase oxygen within the enclosure. In this opposing operation mode, the two cell may somewhat counteract each other and may be less effective.

As shown in FIG. 6, an exemplary environment control system 10 has two electrochemical cells 12, 12' coupled with a conditioner chamber 62 and a separator 58 configured between the oxygen control chamber 60 and the humidity control chamber 70. An oxygen control electrolyzer cell 16 has the anode cathode 40 in fluid communication with the oxygen control chamber 60 and a humidity control electrolyzer cell 17 has the anode 20' in fluid communication with the humidity control chamber 70. The separator membrane, as described herein, allows moisture to be transferred between the oxygen and humidity control chambers, but limits the transfer of oxygen, since it is essentially air impermeable. Therefore, when there is a differential in humidity levels between the oxygen control chamber 60 and the humidity control chamber 70, humidity will pass through the separator 58. The separator may be an ionomer membrane for example. The humidity control chamber 70 has the anode 20' of the second electrochemical cell 12' in fluid communication to reduce humidity and increase oxygen concentration. This reduces humidity level will cause humidity from the oxygen control chamber 60 to pass through the separator and therefore reduce the humidity level in the oxygen control chamber. In this way, the oxygen control chamber may have a reduces oxygen concentration and a reduce humidity concentration, which is desirable for many types of enclosures. A fan 97 may be configure to control the flow from the oxygen control chamber to the enclosure 50, through the enclosure wall 55. An inlet exchange conduit 57 is configured with a filter 67 and the outlet exchange conduit 59 is also configured with a filter 69. A fan 97 or other air moving device is configured to force flow and exchange between the enclosure and the conditioner chamber 62, and specifically the oxygen control chamber 60. A fan and valve may be configured on the oxygen control chamber 60 or the humidity control chamber 70 to allow exchange with the outside environment. The concentration of humidity and/or oxygen may require an air exchange with the outside air, for example. A desiccant 90 and filter 93 are configured to reduce the humidity concentration in the humidity control chamber and may reduce the moisture from air being drawn into the humidity control chamber or may be configured in a circulation loop of the humidity control chamber, as shown in FIG. 8, for example. A desiccant may be replaced periodically as required by the application. A controller 80 may utilize inputs from sensors 83, 84 to control the operation of the environment control system 10.

As shown in FIGS. 7 and 8, an exemplary environment control system 10 has an exchange conduit 61 as an oxygen control chamber 60 with an inlet 57 and outlet 59. The exchange conduit 61 extends within the conditioner chamber, wherein at least a portion of the exchange conduit is configured with a separator 58 to allow moisture to pass from the exchange conduit, or oxygen control chamber, into the humidity control chamber 70 portion of the conditioner chamber 62. In this embodiment, more surface area may be provided for the separator. In addition, the humidity control chamber may be configured with a dehumidification loop 91 that circulates gases from the humidity control chamber through a desiccator 90. A fan 97 is configured to move gasses through the dehumidification loop. As shown in FIG. 8, the exchange conduit 61 is serpentine, to provide additional separator 58 exchange surface area. Again, any number of valves 98 and fans 97 may be used to exchange gasses within the chambers with the outside environment, as described herein. A condenser 64 is also shown in the dehumidification loop. A condenser and/or desiccant or desiccator may be configured in the dehumidification loop.

As shown in FIG. 9, a portion of the humidity control chamber 70 gas is fed to the anode side of the electrochemical cell 12, an oxygen control electrolyzer cell 16 operating as an oxygen depletion electrolyzer cell. The oxygen depletion electrolyzer cell is configured with the cathode 40 in fluid communication with the oxygen control chamber 60 and the humidity control electrolyzer cell 17, acting as a humidity reduction electrolyzer cell, is configured with the anode 20' in fluid communication with the humidity control chamber 70. The humidity control chamber may comprise moisture that can be consumed by the reaction at the anode of the oxygen depletion electrolyzer cell, wherein water is converted to oxygen and protons. A fuel loop 68 is configured to direct humidity control chamber gas to the anode of the oxygen depletion electrolyzer cell. In this way, the moisture can be reduced in the humidity control chamber 70 while providing the necessary fuel to the anode of the oxygen depletion electrolyzer cell. Again, any number of valves 98 and fans 97 may be used to exchange gasses within the chambers with the outside environment, as described herein. A condenser 64 is also shown in the dehumidification loop. A condenser and/or desiccant or desiccator may be configured in the dehumidification loop.

As shown in FIG. 10, an exemplary environment control system 10 has a water chamber 65 with a pervaporation layer 66 between the water chamber and the oxygen control electrolyzer cell. The pervaporation layer may be an ionomer membrane or any other material that allow water vapor to transfer through without any bulk flow of air, as described herein. A condenser 64 is configured condense humidity into liquid water from the conditioner chamber 62. In this embodiment, a single electrochemical cell 12 is utilized to reduce the oxygen concentration in the oxygen control chamber 60 of the conditioner chamber 62, which is in fluid communication with the enclosure 50 through the condenser. The condenser is configured to draw gas from the oxygen control chamber 60. In one embodiment, there is no separator between the oxygen control chamber and the humidity control chamber and the gas fed to the condenser is drawn from the conditioner chamber generally and the electrochemical cell reduces oxygen from this same conditioner cell. However, as shown, the oxygen control chamber is configured with an opening to the condenser, a valve 98 is shown here. The gas in the oxygen control chamber has a reduced oxygen concentration and an increased humidity level, or water content. An oxygen bleed valve 99 may be configured to bleed the gases from the oxygen control chamber or any portion of the conditioner chamber. Gas is drawn into the condenser and the water vapor is condensed and collects in the bottom of the condenser, wherein it can be fed to through a valve 73 to a water chamber 65, or fuel chamber for the oxygen control electrolyzer cell 16 acting as an oxygen depletion electrolyzer cell. This may be a way of providing the water required to the oxygen depletion electrolyzer cell, especially in arid environments. The pervaporation separator 66 keeps any contaminates in the water from fouling or poisoning the catalyst of the anode. A valve may be opened when required to draw in more air to the cathode side of the oxygen reduction electrolyzer cell.

As shown in FIGS. 6 to 10, a MEA air moving device 44 is configured to produce a flow of process air, or forced air onto the anode of the oxygen control electrolyzer cell 16. The forced air may impinge directly onto the anode as shown in FIGS. 6 to 9 or may flow across the MEA, as shown in FIG. 10. As shown in FIGS. 6 to 9 an MEA air moving device 44 is couple with the humidity control electrolyzer cell 17 and configured to produce a flow of process air onto the anode of the humidity control electrolyzer cell. As described herein, the flow of process air onto the anode can greatly improve the performance of the cell.

As shown in FIG. 11, an exemplary environment control system 10 has an enclosure filter 52 to the enclosure 50, and inlet and outlet filters to the conditioner chamber 62. An activated carbon may be used in the enclosure filter to protect the MEA from contaminates inside the enclosure. The conditioner chamber may also comprise inlet and/or outlet filters to protect the MEA from contaminants from the ambient air. This humidification control system has a single electrochemical cell 12, a humidification control electrochemical cell 17 that may be run with the anode or the cathode in fluid communication with the enclosure. Likewise, it may be an Oxygen control electrochemical cell.

As shown in FIGS. 12 and 13, an exemplary environment control system 10 is configured to control the environment within a safe 110. The front of the safe, as shown in FIG. 12 has a door 111 to form an enclosure 50. The environment control system 10 is configured on the back side of the safe, as shown in FIG. 13, and may control the level of oxygen and/or humidity within the safe enclosure.

As shown in FIGS. 14 and 15, an exemplary environment control system 10 is configured to control the environment within a refrigerator 119, in this a wine cooler. The front of the wine cooler, as shown in FIG. 14 has a door 11 to form an enclosure 50. The environment control system 10 is configured on the back side of the wine cooler, as shown in FIG. 15, and may control the level of oxygen and/or humidity within the refrigerator.

As shown in FIGS. 16 and 17, an exemplary environment control system 10 is configured to control the environment within a humidor 114. The top of the humidor, as shown in FIG. 16 has a door 11 to form an enclosure 50. The environment control system 10 is configured on the bottom of the humidor, as shown in FIG. 17, and may control the level of oxygen and/or humidity within the humidor enclosure.

As shown in FIG. 18, an exemplary environment control system 10 is configured to control the environment of growing enclosure 117, such as a vase or pot for growing a plant. The environment control system 10 may control the humidity and/or oxygen level of the space below the plant or dirt within the enclosure 50.

As shown in FIG. 19, an exemplary environment control system 10 has two electrochemical cells 12,12' for placement of an enclosure thereon.

FIG. 20 shows a person 101 sleeping with the aid of a Positive Airway Pressure (PAP) device 100. The PAP device or breathing device has a flow generator (PAP machine) 102 that provides the airflow to the hose 104 that connects the patient interface 106. The hose connects the flow generator (sometimes via an in-line humidifier) to the interface 106. An interface includes, but is not limited to, a nasal or full face mask, nasal pillows, or less commonly a lip-seal mouthpiece, provides the connection to the user's airway or respiratory system, such as through the nose or mouth. An exemplary environment control system 10 is attached to the flow generator 102 or enclosure of the flow generator 50 and may be used to increase the level of oxygen and/or humidity within the pressurized flow delivered to the person. A PAP device, as used herein, includes all of the variations of breathing aid devices described herein.

As shown in FIG. 21, an exemplary electrolyzer cell comprises a filter 94, MEA fan 44, housing components 43, 43', flow fields 38, 38', current collector 33, membrane electrode assembly 30, gas diffusion media 39, and a gasket 45. This assembly has a fan configured to blow air directly onto the MEA 30. As described herein, this improves performance of the MEA.

As shown in FIG. 22, an exemplary environment control device 10 comprises an oxygen control electrolyzer cell 16 and a humidity control electrolyzer cell 17 configured around a conditioner chamber 62. An MEA air moving device 44, such as a fan, is configured to produce a flow of process air 46, which is a flow of forced air, onto the anode of the oxygen control electrolyzer cell 16. As described herein, this greatly increases the efficiency of the oxygen control electrolyzer cell 16. The air moving device 44 is coupled directly to the MEA and has close proximity to the anode which may be important for improved efficiency. An MEA air moving device 44', such as a fan, is configured between the humidity control electrolyzer cell 17 and the conditioner chamber 62 to produce a flow of process air 46' onto the anode of the humidity control electrolyzer cell 17. This fan may be configured within the conditioner chamber with the MEA of the humidity control electrolyzer cell being sealed against the conditioner chamber. Electrical contacts are coupled to each of the electrolyzer cells to provide a potential across the anode and cathode.

FIG. 23 shows a graph an enclosure temperature and humidity with and without a fan blowing onto the anode of a humidity control electrolyzer. The data shows that the humidity was reduced much more quickly when the electrolyzer was operated with a fan blowing directly onto the MEA to produce a flow of process air, or forced air, onto the anode of the humidity control electrolyzer cell.

Referring now to FIGS. 24 and 25, an exemplary oxygen control electrolyzer cell 16, is configured with an MEA air moving device 44, such as a fan, configured to produce a flow of process air 46 onto the anode 20 of the membrane electrode assembly 30. This assembly may be an integral MEA 149 as the MEA may be bonded to the housing by an adhesive as shown in FIG. 26, FIGS. 27 and 28. A water chamber 65 is configured around a forced air opening 48 to allow the forced air to impinge directly onto the MEA or anode 20 of the MEA. A pervaporation layer 66 that allows the transport of water therethrough, but prevents the bulk flow of air, extends around the forced air opening to provide water or moisture to the MEA. A gasket 71 seals the pervaporation layer to the MEA. The flow of process air impinges directly onto the anode side 21 of the MEA 30 and the cathode side 41 or cathode 40 of the MEA may be sealed to a conditioner chamber, not shown. A data interface 86 is configured to allow coupling of a data storage and/or a data transmitter. Data related to the environment control device, such as humidity level, oxygen level, temperature, MEA voltage potential and the like may be stored and/or transferred to remote location. A fill port 63 for receiving fluid, such as water for hydrating the ion conducting media, such as an ionomer is shown. The port may receive water or fluid from a condenser of the conditioner chamber, or it may be manually filled, or attached to an automatic filing system, wherein when the water chamber 65 drops below a certain level, a valve on the fill port fills the water chamber above a threshold level.

Referring now to FIGS. 26 to 29, a membrane electrode assembly 30 may be an integral membrane electrode assembly that is bonded to the housing 47 by an adhesive 148, and whereby the MEA is not detachably attachable to the housing after adhesive attachment. An exemplary integral MEA is coupled to a housing 47 and may comprise a discrete current collector 33, 33' instead of a flow field and/or current collector that extends across the surface area of the electrodes or MEA assembly. An exemplary discrete current collector is a strip of material having a width that is at least double a thickness, and wherein the thickness is no more than 2 mm. A membrane electrode assembly 30 may be formed by attaching a housing 47 to the membrane electrode assembly with an adhesive 145 and/or a gasket-adhesive 148 and the application of heat and/or pressure, as indicated by the bold large arrows in FIG. 27. The adhesive 145 may be a film of adhesive or may be a discontinuous adhesive. The adhesive may be coupled with a gasket, a gasket adhesive 148 that extends around the electrode, such as the anode and cathode and may be bonded to the ionomer or ion conducting layer. FIG. 26 shows a perspective view of a membrane electrode assembly attached to a housing. The adhesive is configured between the housing 47, 47' and the catalyst 23, 23'. Heat and/or pressure, as indicated by the large bold arrows in FIG. 27 may be used to cause the adhesive to melt or soften to bond the housing to the membrane electrode assembly 30. The adhesive may be a thermoplastic and may comprise an ionomer such as perfluorosulfonic acid. In an exemplary embodiment, the adhesive is discontinuous, such as a sheet or film with apertures therethrough, such as a net or screen of material and comprises an ionomer.

As shown in FIGS. 26 and 28, the housing is attached to the MEA 30 by the adhesive 145. The gasket-adhesive extends around the anode 20 and cathode 40 and is attached between the housing and the proton conducing layer 32, comprising an ionomer. A current collector 33, 33' extends out from the MEA and housing and is contact with the anode 20 and cathode 40 respectively. The integral MEA assembly 149, comprising a MEA 30 coupled to a housing 47 may be small in size, such as less than 10 cm$^2$, less than about 5 cm$^2$, or even less than 2 cm$^2$. A small integral MEA assembly may be used in mini-applications and may be used as a humidification control device as described herein, or in any of the environmental control systems as described herein, wherein humidity and/or oxygen levels are controlled or adjusted by this device. Therefore, the current collector may be a wire or strip of electrically conductive material that contacts the electrode, anode or cathode and extends out from the MEA assembly. The size of the MEA may be small and therefore there may be little resistance across the electrode to the current collector.

The housing 47 may comprise a plurality of opening 48 to allow airflow to the MEA. As shown in FIGS. 27 and 28, the adhesive 145 and/or the gasket adhesive 148 may be configured to align with the housing over the electrode, whereby the adhesive does not impede or block airflow through the openings to the electrode. The adhesive may be a comprise a cover layer and the cover layer may be peeled off for adhering the adhesive or gasket-adhesive to the housing and/or the proton conducting layer.

The integral MEA assembly 149 may be coupled over an opening of an enclosure and may separate an inner volume of the enclosure with an outside volume or ambient air of the enclosure. The integral MEA assembly may be provided a current and voltage to control humidity within an enclosure and/or oxygen levels. The integral MEA assembly may be a vent over an opening of an enclosure and be an active vent, controlling the humidity and/or oxygen level within the enclosure.

The integral MEA may be attached to an enclosure and may comprise a flexible housing, such as a fabric, including a woven or non-woven, a netting material or screen material. The integral MEA may be coupled to a housing on one side and to an enclosure by an adhesive on the opposing side.

Fluid communication, as used herein, means that gasses can flow to and from the two items described to be in fluid communication. For example, the cathode of an oxygen reduction electrolyzer cell may be in fluid communication with the oxygen control chamber, wherein the reaction products from the anode can freely flow into the oxygen control chamber.

The electrochemical cells, 12 shown in the figures may run as electrolyzer cells, as described herein that perform electrolysis of water, wherein water is broken down on the anode into protons and oxygen and reformed on the cathode with the protons and oxygen.

The electrochemical cells can be operated at higher potentials to produce ozone, which may be used to clean and disinfect the enclosure.

When an electrochemical cell is operated at a potential above 1.2 volts, electrolysis of water will occur and when operated above 2.08 volts, ozone may be produced.

Dehumidification device, as used herein, is a device that reduces the humidity level or RH and includes, but is not limited to, a desiccant or desiccator employing a desiccant, a condenser and a humidity reduction electrolyzer cell.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An environment control system that is coupled with an enclosure and comprises:

a) an oxygen control electrolyzer cell,
wherein the oxygen control electrolyzer cell comprises:
  i) an ion exchange medium;
  ii) an anode;
  iii) a cathode;
wherein the anode and cathode are configured on opposing sides of the ion exchange medium;
wherein the oxygen control electrolyzer cell is an integral membrane electrode assembly (MEA) comprising:
  a housing attached to said oxygen control electrolyzer cell;
  an anode opening in the housing to provide a flow of air to the anode;
  a cathode opening in the housing to provide a flow of air to the cathode;
b) a controller that is coupled with a power source and the oxygen control electrolyzer cell to control electrical potential across the anode and the cathode;
  wherein an oxygen concentration within the enclosure is controlled by the oxygen control electrolyzer cell;
d) a conditioning chamber in fluid communication with the enclosure;
e) a humidity control chamber;
wherein the oxygen control electrolyzer cell is fluid communication with the conditioning chamber; and
f) a separator configured between the conditioning chamber and the humidity chamber;
wherein the separator comprises ionomer and is substantially air impermeable having no bulk flow of gas therethrough.

2. The environment control system of claim 1, wherein the oxygen control electrolyzer cell is an oxygen reduction electrolyzer cell having the cathode in fluid communication with the enclosure; and
  wherein said power source is coupled with the anode and cathode to provide an electrical potential across the anode and the cathode to initiate electrolysis of water, wherein water is reacted to form oxygen and protons on the anode and said protons react with oxygen at the cathode to form cathode side water, thereby reducing oxygen concentration in the enclosure.

3. The environmental control system of claim 1, further comprising a humidity control device that is fluid communication with the humidity control chamber and comprises a humidity control electrolyzer cell,
  wherein the humidity control electrolyzer cell comprises:
    i) an ion exchange medium;
    ii) an anode;
    iii) a cathode;
  wherein the anode and cathode of the humidity control electrolyzer cell are configured on opposing sides of the ion exchange medium of the humidity control electrolyzer cell.

4. The environment control system of claim 1, wherein the oxygen control electrolyzer cell is an oxygen elevation electrolyzer cell having the anode in fluid communication with the enclosure; and
  wherein said power source is coupled with the anode and cathode to provide an electrical potential across the anode and the cathode to initiate electrolysis of water, wherein water is reacted to form oxygen and protons on the anode and said protons react with oxygen at the cathode to form cathode side water, thereby increasing oxygen concentration in the enclosure.

5. The environment control system of claim 4, further comprising:
  an oxygen control chamber in fluid communication with the enclosure;
  wherein the oxygen control electrolyzer cell is fluid communication with the oxygen control chamber;
  wherein the separator is configured between the oxygen control chamber and the humidity control chamber for transporting moisture between said oxygen control chamber and said humidity control chamber;
    wherein the separator comprise ionomer and is substantially air impermeable.

6. The environment control system of claim 5 comprising a humidity control device that is fluid communication with the humidity control chamber and comprises a humidity control electrolyzer cell,
  wherein the humidity control electrolyzer cell comprises:
    i) an ion exchange medium;
    ii) an anode;
    iii) a cathode;
  wherein the anode and cathode of the humidity control electrolyzer cell are configured on opposing sides of the ion exchange medium of the humidity control electrolyzer cell.

7. The environment control system of claim 1, wherein the integral membrane electrode assembly comprises adhesive bonding the membrane electrode assembly to said housing of the integral membrane electrode assembly.

8. The environment control system of claim 7, wherein the adhesive is a pressure sensitive adhesive.

9. The environment control system of claim 7, wherein the adhesive is a thermoplastic adhesive and wherein the thermoplastic adhesive is melted to adhere the MEA to the housing.

10. The environment control system of claim 7, wherein the adhesive is couple to a gasket to form a gasket-adhesive that extends around an electrode of the MEA.

11. The environment control system of claim 7, wherein the housing of the integral membrane electrode assembly is a rigid housing.

12. The environment control system of claim 7, wherein the housing of the integral membrane electrode assembly is an air permeable fabric.

13. The environment control system of claim 12, wherein the housing of the integral membrane electrode assembly is a non-woven fabric.

14. The environment control system of claim 1, wherein the MEA comprises a discrete current collector that extends out from a contact with at least one of the anode or cathode.

15. The environment control system of claim 1, wherein the electrode area of the anode or cathode is no more than about 20 cm$^2$.

16. An environment control system that is coupled with an enclosure and comprises:
  a) an oxygen control electrolyzer cell,
  wherein the oxygen control electrolyzer cell comprises:
    i) an ion exchange medium;
    ii) an anode;
    iii) a cathode;
  wherein the anode and cathode are configured on opposing sides of the ion exchange medium;
  b) a controller that is coupled with a power source and the oxygen control electrolyzer cell to control electrical potential across the anode and the cathode;
    wherein an oxygen concentration within said enclosure is controlled by the oxygen control electrolyzer cell;
  c) an oxygen control chamber coupled to the oxygen control electrolyzer cell and comprising an exchange conduit;

d) a conditioning chamber, wherein at least a portion of the exchange conduit is configured within the conditioning chamber;

wherein at least a portion of the exchange conduit is configured with a separator to transfer moisture from the exchange conduit into the conditioner chamber;

wherein the separator comprises ionomer and is substantially air impermeable having no bulk flow of gas therethrough.

17. The environment control system of claim 16, wherein the oxygen control electrolyzer cell is an oxygen reduction electrolyzer cell having the cathode in fluid communication with the enclosure; and wherein said power source is coupled with the anode and cathode to provide an electrical potential across the anode and the cathode to initiate electrolysis of water, wherein water is reacted to form oxygen and protons on the anode and said protons react with oxygen at the cathode to form cathode side water, thereby reducing oxygen concentration in the enclosure.

18. The environmental control system of claim 17 further comprising a humidity control device in fluid that is in communication with the conditioning chamber.

19. The environment control system of claim 18, wherein the humidity control device comprises a humidity control electrolyzer cell comprising:
   i) an ion exchange medium;
   ii) an anode;
   iii) a cathode;
   wherein the anode and cathode of the humidity control electrolyzer cell are configured on opposing sides of the ion exchange medium of the humidity control electrolyzer cell.

* * * * *